(12) United States Patent  
van der Burg et al.

(10) Patent No.: US 8,777,990 B2
(45) Date of Patent: Jul. 15, 2014

(54) KNOTLESS SUTURE ANCHOR FOR SOFT TISSUE REPAIR AND METHOD OF USE

(75) Inventors: Erik van der Burg, Los Gatos, CA (US); Nathaniel Cohen, Los Gatos, CA (US); Christopher Feezor, San Jose, CA (US); Christopher T. Cheng, Mountain View, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 802 days.

(21) Appl. No.: 12/206,643

(22) Filed: Sep. 8, 2008

(65) Prior Publication Data

US 2010/0063542 A1 Mar. 11, 2010

(51) Int. Cl.
*A61B 17/04* (2006.01)

(52) U.S. Cl.
USPC .............. 606/232; 606/300; 24/71.1; 24/909

(58) Field of Classification Search
USPC ............. 606/74, 103, 232, 300; 24/71.1, 269, 24/909
See application file for complete search history.

(56) References Cited

U.S. PATENT DOCUMENTS

| | | | | |
|---|---|---|---|---|
| 1,088,892 | A | * | 3/1914 | Forman .......................... 411/418 |
| 2,429,675 | A | * | 10/1947 | Eypper ....................... 242/388.1 |
| 3,845,772 | A | | 11/1974 | Smith |
| 3,988,007 | A | * | 10/1976 | Freiburger, Jr. ............... 24/68 R |
| 4,750,492 | A | | 6/1988 | Jacobs |
| 4,870,957 | A | | 10/1989 | Goble et al. |
| 4,884,572 | A | | 12/1989 | Bays et al. |
| 4,976,715 | A | | 12/1990 | Bays et al. |
| 5,102,414 | A | | 4/1992 | Kirsch |
| 5,152,790 | A | | 10/1992 | Rosenberg et al. |
| 5,236,445 | A | | 8/1993 | Hayhurst et al. |
| 5,268,001 | A | | 12/1993 | Nicholson et al. |
| 5,429,641 | A | | 7/1995 | Gotfried |
| 5,480,403 | A | * | 1/1996 | Lee et al. ....................... 606/232 |
| 5,486,197 | A | | 1/1996 | Le et al. |
| 5,498,265 | A | | 3/1996 | Asnis et al. |
| 5,527,341 | A | | 6/1996 | Gogolewski et al. |

(Continued)

FOREIGN PATENT DOCUMENTS

EP 1862127 A1 5/2007
WO 2008/011417 A2 1/2008

OTHER PUBLICATIONS

Partial European Search Report, EP 09175847, dated Feb. 23, 2010.

(Continued)

*Primary Examiner* — David Eastwood
(74) *Attorney, Agent, or Firm* — Lerner, David, Littenberg, Krumholz & Mentlik, LLP

(57) ABSTRACT

A knotless suture anchor provides a method for securing soft tissue to a rigid structure such as bone. The anchor has an inner member that receives suture thread and rotates within an outer tubular member. As the inner member rotates, the suture thread is wrapped onto the inner member thereby increasing contact with the outer tubular member which applies pressure to the wrapped suture thread to retain it in position on the inner member while simultaneously and adjustably tensioning the suture thread. A ratchet prevents undesirable counter-rotation, although the ratchet can be released to permit loosening of the suture thread. Also described is a suture bridge and suture platform for providing further stabilization of a tendon. A method for repairing rotator cuff tears is also described.

30 Claims, 16 Drawing Sheets

(56) References Cited

U.S. PATENT DOCUMENTS

| | | | |
|---|---|---|---|
| 5,534,011 | A | 7/1996 | Greene, Jr. et al. |
| 5,545,180 | A * | 8/1996 | Le et al. .......... 606/232 |
| 5,584,835 | A | 12/1996 | Greenfield |
| 5,601,557 | A | 2/1997 | Hayhurst |
| 5,618,314 | A | 4/1997 | Harwin et al. |
| 5,649,931 | A | 7/1997 | Bryant et al. |
| 5,667,513 | A | 9/1997 | Torrie et al. |
| 5,725,529 | A | 3/1998 | Nicholson et al. |
| 5,782,864 | A | 7/1998 | Lizardi |
| 5,843,127 | A | 12/1998 | Li |
| 5,849,004 | A | 12/1998 | Bramlet |
| 5,906,617 | A | 5/1999 | Meislin |
| 5,957,953 | A | 9/1999 | DiPoto et al. |
| 5,964,764 | A * | 10/1999 | West et al. ........ 606/232 |
| 6,039,741 | A | 3/2000 | Meislin |
| 6,077,267 | A | 6/2000 | Huene |
| 6,129,728 | A | 10/2000 | Schumacher et al. |
| 6,139,565 | A | 10/2000 | Stone et al. |
| 6,238,435 | B1 | 5/2001 | Meulink et al. |
| 6,330,845 | B1 | 12/2001 | Meulink |
| 6,485,503 | B2 | 11/2002 | Jacobs et al. |
| 6,554,852 | B1 | 4/2003 | Oberlander |
| 6,626,910 | B1 | 9/2003 | Hugues |
| 6,641,597 | B2 | 11/2003 | Burkhart et al. |
| 6,666,877 | B2 | 12/2003 | Morgan et al. |
| 6,682,549 | B2 | 1/2004 | Bartlett |
| 6,689,154 | B2 | 2/2004 | Bartlett |
| 6,692,516 | B2 | 2/2004 | West, Jr. et al. |
| 6,770,084 | B1 | 8/2004 | Bain et al. |
| 6,884,248 | B2 | 4/2005 | Bolduc et al. |
| 6,887,259 | B2 | 5/2005 | Lizardi |
| 6,893,452 | B2 | 5/2005 | Jacobs |
| 6,923,830 | B2 | 8/2005 | Michelson |
| 6,926,718 | B1 | 8/2005 | Michelson |
| 7,022,129 | B2 | 4/2006 | Overaker et al. |
| 7,037,324 | B2 | 5/2006 | Martinek |
| 7,081,126 | B2 | 7/2006 | McDevitt et al. |
| 7,083,638 | B2 | 8/2006 | Foerster |
| 7,090,690 | B2 | 8/2006 | Foersster et al. |
| 7,235,100 | B2 | 6/2007 | Martinek |
| 7,309,346 | B2 | 12/2007 | Martinek |
| 7,381,213 | B2 | 6/2008 | Lizardi |
| 7,416,556 | B2 | 8/2008 | Jackson |
| 7,959,649 | B2 | 6/2011 | Burkhart |
| 2002/0161401 | A1 * | 10/2002 | Steiner .......... 606/232 |
| 2002/0169478 | A1 | 11/2002 | Schwartz et al. |
| 2003/0004545 | A1 | 1/2003 | Burkhart et al. |
| 2003/0120309 | A1 * | 6/2003 | Colleran et al. ........ 606/232 |
| 2003/0229361 | A1 * | 12/2003 | Jackson .......... 606/144 |
| 2003/0233100 | A1 | 12/2003 | Santarella et al. |
| 2004/0138706 | A1 * | 7/2004 | Abrams et al. ........ 606/232 |
| 2004/0220574 | A1 | 11/2004 | Pelo et al. |
| 2005/0081339 | A1 * | 4/2005 | Sakabayashi .......... 24/128 |
| 2005/0090827 | A1 | 4/2005 | Gedebou |
| 2005/0090862 | A1 | 4/2005 | McDevitt et al. |
| 2005/0192577 | A1 | 9/2005 | Mosca et al. |
| 2005/0240222 | A1 | 10/2005 | Shipp |
| 2005/0267478 | A1 | 12/2005 | Corradi et al. |
| 2006/0004364 | A1 | 1/2006 | Green et al. |
| 2006/0100630 | A1 | 5/2006 | West |
| 2006/0135996 | A1 | 6/2006 | Schwartz et al. |
| 2006/0200199 | A1 * | 9/2006 | Bonutti et al. ........ 606/232 |
| 2006/0201519 | A1 | 9/2006 | Frazier et al. |
| 2006/0271105 | A1 | 11/2006 | Foerster et al. |
| 2007/0005068 | A1 | 1/2007 | Sklar |
| 2007/0038221 | A1 | 2/2007 | Fine et al. |
| 2007/0043378 | A1 | 2/2007 | Kumar et al. |
| 2007/0156176 | A1 * | 7/2007 | Fanton et al. .......... 606/232 |
| 2007/0167950 | A1 | 7/2007 | Tauro et al. |
| 2007/0250064 | A1 | 10/2007 | Darois et al. |
| 2007/0260259 | A1 | 11/2007 | Fanton et al. |
| 2007/0276412 | A1 | 11/2007 | Catanese et al. |
| 2008/0009904 | A1 | 1/2008 | Bourque et al. |
| 2008/0021474 | A1 | 1/2008 | Bonutti et al. |
| 2008/0033486 | A1 | 2/2008 | Whittaker et al. |
| 2008/0086138 | A1 | 4/2008 | Stone et al. |
| 2008/0140118 | A1 | 6/2008 | Martinek |
| 2009/0043337 | A1 | 2/2009 | Martin |
| 2009/0171400 | A1 | 7/2009 | van der Burg et al. |
| 2010/0094355 | A1 | 4/2010 | Trenhaile |
| 2010/0100127 | A1 | 4/2010 | Trenhaile |
| 2011/0245869 | A1 | 10/2011 | Burkhart |

OTHER PUBLICATIONS

Provisional Application for U.S. Letters Patent, U.S. Appl. No. 60/954,558, filed Aug. 7, 2007, entitled Suture-Retaining Device and Anchor.

Rockwood C., et al., The Shoulder, Saunders, 2004; 820-821.

European Search Report, EP10164525, dated Aug. 6, 2010.

Partial European Search Report, EP 09169742, dated Jan. 8, 2010.

\* cited by examiner

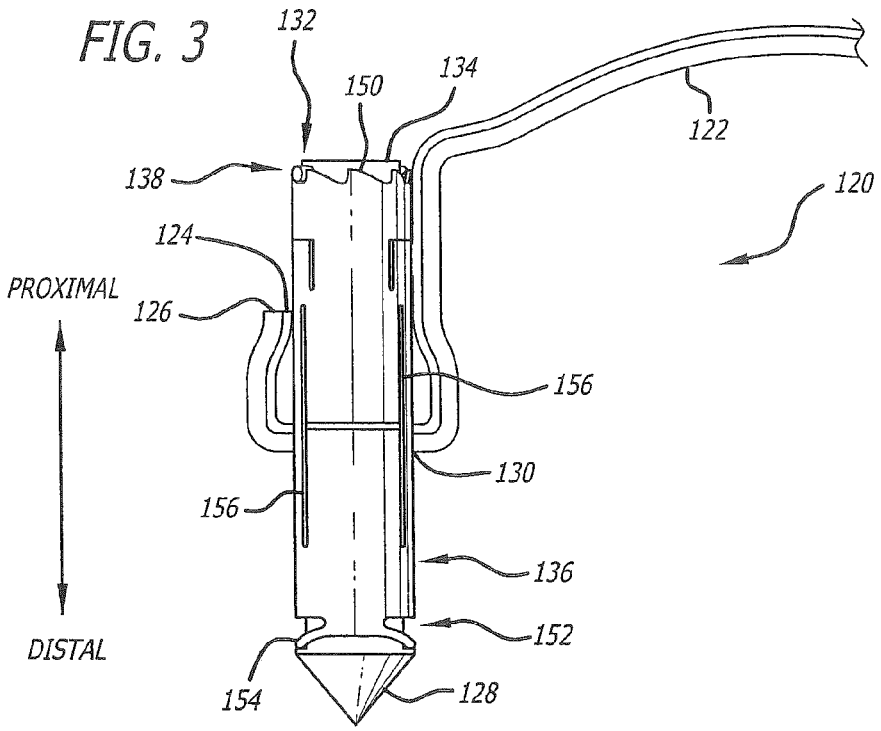
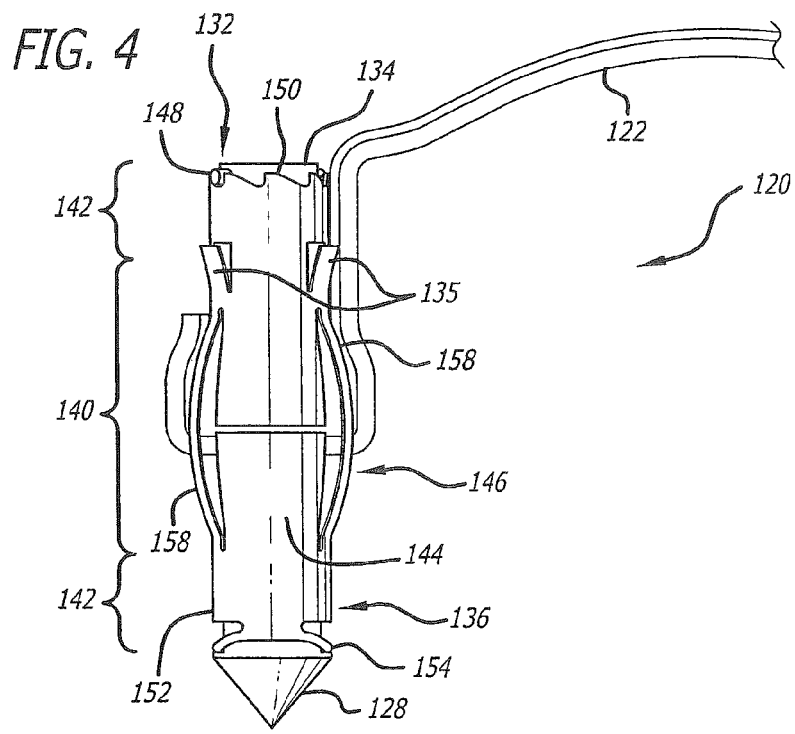

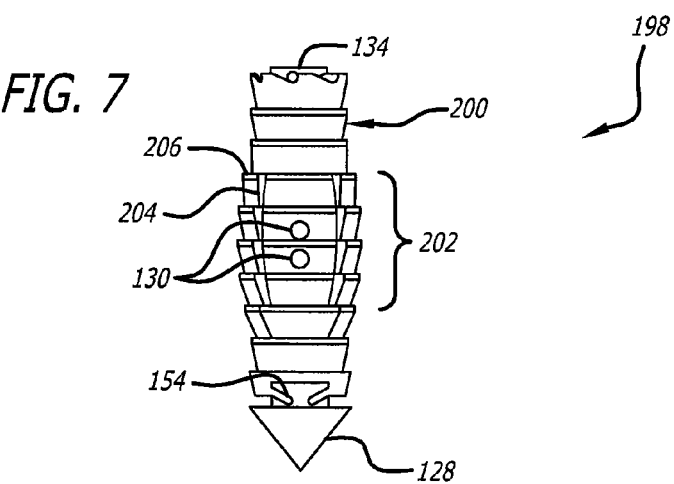
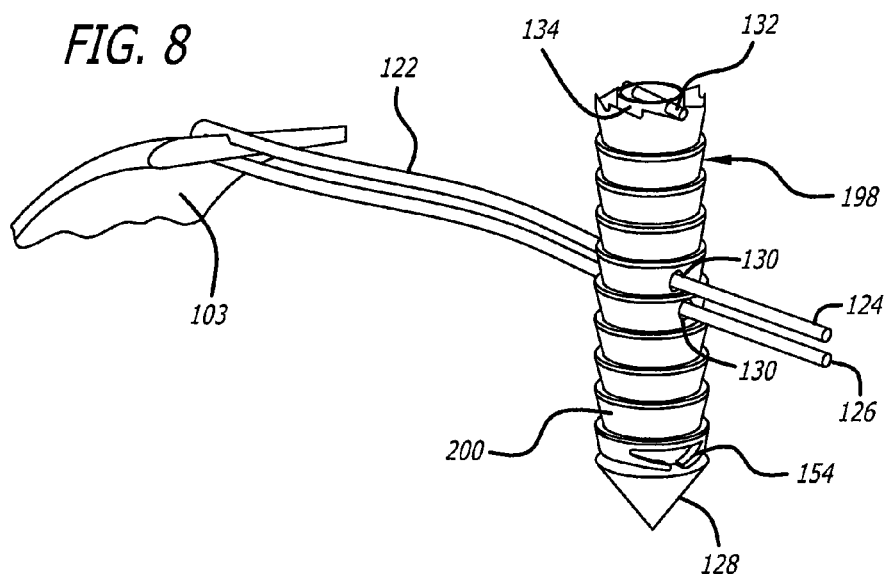

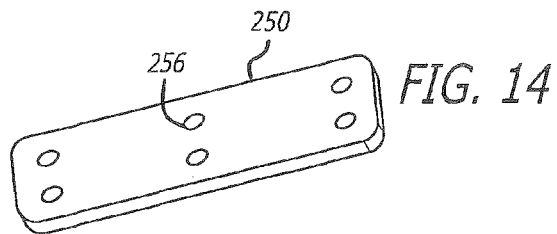
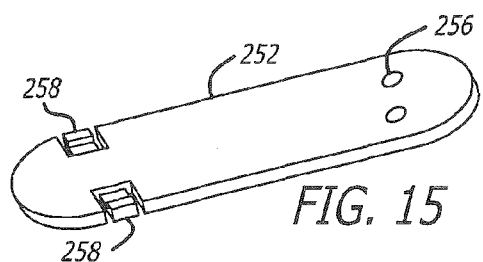
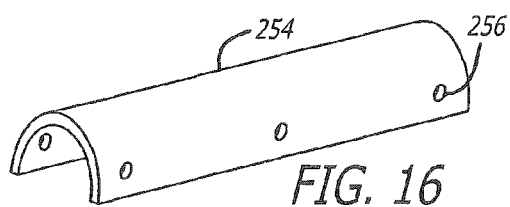
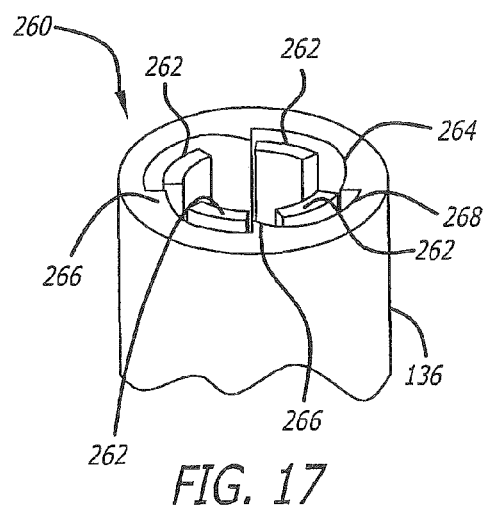
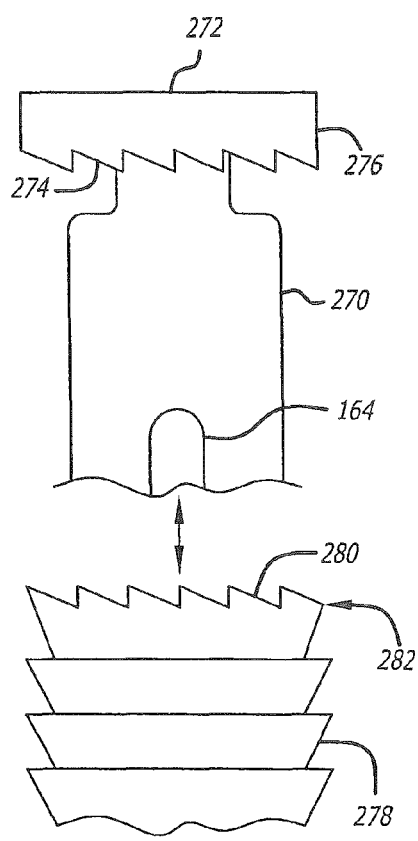

KNOTLESS SUTURE ANCHOR FOR SOFT TISSUE REPAIR AND METHOD OF USE

FIELD OF THE INVENTION

The present invention relates to medical devices and procedures, and more particularly, to methods and devices for approximation of soft tissue to a rigid material such as bone.

BACKGROUND OF THE INVENTION

There are many medical procedures where a surgeon needs to attach soft tissue to bone. The soft tissue can be tendon or other connective tissue. One very common example of this is rotator cuff repair where a portion or all of the rotator cuff is torn or detached from the humerus. When the rotator cuff tears from the humerus, the result is pain and loss of function. Rotator cuff disease affects a large number of people worldwide, affecting many people over the age of forty. Some studies have shown a prevalence of approximately 30% in people over the age of forty (Rockwood C., et al., *The Shoulder*, Saunders, 2004; 820-821). It is estimated that as many as 17 million people in the United States may be at risk for pain and dysfunction as a result of rotator cuff injuries. While the majority of people are asymptomatic, a significant subset goes on to have disability. One study in patients with rotator cuff tears in one shoulder found that 50% of these patients who had an asymptomatic rotator cuff tear in the other shoulder went on to become symptomatic (Yamaguchi, K., et al., *J. Shoulder Elbow Surg.*, 2001;10:199-203).

The prevalence of symptomatic rotator cuff disease is reflected in the large numbers of surgical repair for this condition. Rotator cuff repair is one of the most common orthopedic procedures performed. When a patient presents with a significant rotator cuff tear, surgical repair is performed. The goal of surgical repair of the rotator cuff is to secure the tendon to the bone in a stabile manner so that the tendon can reattach to the bone and can heal. If the tendon is not stabile and oscillation or micro-motion between the tendon and bone develops, the healing process will be interrupted. In this situation, it is less likely that the tendon will heal properly to the bone, resulting in a re-tear. Thus, the more stabile the repair, the more successfully the tendon will heal to the bone.

Rotator cuff repair is performed open or arthroscopically, most often using suture anchors. These have one point of fixation with either one suture or several sutures attached for reattaching the tendon to the bone. While arthroscopic repair is less painful and thus more attractive to patients, many surgeons continue to perform open rotator cuff repairs. Much of the reason for this is due to the challenge of arthroscopic shoulder surgery. There is a significant learning curve in gaining the skills to be able to manage multiple strands of suture in a relatively small field of view, passing these through the tendon and knotting the sutures in the process of tying the tendon into apposition with the bone. Many of these techniques can be relatively time-consuming when compared with open surgery.

There is a growing body of literature showing that surgical rotator cuff repair has a high rate of failure. Failure of rotator cuff repairs is a well-described complication of rotator cuff repairs, both open and arthroscopic. For example, Gerber et al. found a re-tear rate of 20% following isolated repair of the supraspinatus. Bishop found a re-tear rate of 31% in arthroscopic and 47% in patients undergoing open repair (Bishop J., et al. *Cuff integrity after arthroscopic versus open rotator cuff repair: A prospective study*, J. Shoulder Elbow Surg., 2006; 15:290-299). Galatz found an even higher re-tear rate in larger tears (Galatz, L., et al., *The outcome and repair integrity of completely arthroscopically repaired large and massive rotator cuff tears*, J. Bone Joint Surg. Am., 2004;86A: 219-24). Tendon-to-bone reattachment in a rotator cuff repair procedure can fail by a number of means. In a review of failed rotator cuff surgeries evaluated at re-operation, Cummins cited as one of the weak links in the repair, the suture-tendon interface (Cumins, C. A., et al., *Mode of failure for rotator cuff repair with suture anchors identified at revision surgery*, J. Shoulder Elbow Surg., 2003 March-April;12(2):128-33). To reduce the load on any one suture, (i.e., greater distribution of loads) suture anchors used in tendon repair have begun to add multiple sutures to each suture anchor. Burkhart illustrates that the load on each suture diminishes as the number of sutures holding the tendon in place increases (Burkhart, S. S., et al., *A stepwise approach to arthroscopic rotator cuff repair based on biomechanical principles*, Arthroscopy, 2000 January-February; 16 (1):82-90). Kim demonstrated less strain and greater tendon-bone stability in repairs made with multi row (4 fixation points) than with single row (2 fixation points). However, even in the repairs made with 4 fixation points, slippage (oscillation and micro-motion) between the tendon and bone was greater than 3.0 mm after just 200 cycles of physiological loading (Kim, D., et al., *Biomechanical comparison of a single-row versus double row suture anchor technique for rotator cuff repair*, Am. J. Sports Med., 2006; 34;407).

FIG. 1 illustrates a common prior art configuration for attaching tendon to bone. A suture anchor 102 with a pre-attached suture 105 is first driven into the cortical shell 100 and then the cancellous portion 101 of the bone 110, after which one or both of the ends of the suture line 105 are threaded through the tendon 103. The two ends of the suture line 105 are then connected with any one of a variety of knot types 111 to bring the tendon 103 in direct contact, or apposition, with the bone 110. In tendon repair, it is a common practice to mechanically abrade or shave the cortical shell 100 to achieve a bleeding surface. It is believed that a bleeding surface will promote more rapid healing of the tendon to the bone. Stabile apposition between the tendon and bone will promote healing while micro-motion or oscillation between the tendon and the bone may disrupt the healing of the tendon to the bone. In current tendon repair techniques, stability between the tendon and the bone largely comes from the compression the suture can apply between the tendon and bone.

The objective with tendon repair is for the connection between the tendon 103 and bone 110 to remain stabile when physiological lateral force F 108 is applied. FIG. 2 depicts how a position gap 104 may form when physiological lateral force F 108 is applied to the tendon 103 when only sutures are used to apply downward compressive force to secure the tendon to the bone. As the force F 108 exceeds the frictional forces between the tendon and bone and that applied by the suture, the tendon slips along the interface between the tendon and the bone and causes the flexible, non-rigid suture 105 to further compress the tendon and rotate in the direction of the applied force F until a new force equilibrium is achieved. Thus, the undesired oscillation that results in position gap 104 is formed. Such a gap interferes with the healing of the tendon to the bone and may compromise the repair process to an extent that it becomes unsuccessful. Such force F 108 may be applied by the patient using his or her humerous before full reattachment and healing of the tendon 103 to the bone 110 has occurred.

In facilitating or augmenting tendon to bone fixation in surgical rotator cuff repair, typically sutures are passed through the torn tendon a distance medially to the tear that will be sufficient to provide enough tendon to cover the greater tuberosity of the humeral bone. Tension is then applied to the sutures to pull the tendon laterally over the area of the greater tuberosity, and mattress style knots are tied in the sutures gripping the tendon to appose the tendon to the humeral bone. The ends of the sutures are then stretched laterally over the tendon, stabilizing it to the greater tuberosity, and with a knotless anchor, fixed and tensioned to the bone at a position lateral to the tear. As force F is applied to the tendon, the lateral fixation points will stabilize the mattress knots resulting in less gap as shown in FIG. 2. However, due to limitations in their design, current knotless anchors used for lateral fixation do not always adequately fix and tension the suture to the bone or are overly complicated to use, resulting in the potential for inadequate lateral fixation, possibly resulting in the formation of the gap shown in FIG. 2.

Thus what is needed is a tendon to bone fixation method and device that will reliably and simply enhance the stability of the tendon to bone interface which in turn will minimize gap formation and tendon/bone micro-motion and provide a greater opportunity for the tendon to reattach to the bone to heal properly.

SUMMARY OF THE INVENTION

The present invention addresses the difficulty with adequately stabilizing the apposition of soft tissue to bone in soft tissue repair. A knotless suture anchor is provided to adjustably apply tension to a suture engaged with soft tissue to result in better suture control. The anchor is especially effective in a rotator cuff repair.

In one aspect of the invention, a knotless suture anchor for implanting in bone comprises an outer tubular member having a distal end, a proximal end, and an outer wall, the outer wall having an outer dimension selected so that the outer tubular member will be retained within the bone, the outer tubular member having an inner wall, an inner member is rotatably disposed within the outer tubular member, the inner member having an outer diameter, and the inner member and the outer tubular member each having an aperture for receiving a suture thread, wherein the outer diameter of the inner member is selected to be large enough such that as the inner member having a suture thread received by its aperture is rotated, the suture thread is drawn through the aperture of the outer tubular member and wraps onto the inner member thereby increasing the effective diameter of the inner member with the wrapped suture thread coming into contact with the inner wall of the outer tubular member, such contact exerting an inward force on the wrapped suture thread to maintain it in position on the inner member.

In more detailed aspects, the outer dimension of the outer tubular member has a friction fit with the bone in which it is positioned. The outer surface of the outer tubular member includes engagement features formed thereon that engage the bone to retain the anchor.

In other aspects, the knotless suture anchor further comprises a ratcheting mechanism mounted to the inner member and the outer tubular member configured to permit rotation of the inner member in a first direction in relation to the outer tubular member while preventing rotation of the inner member in a second direction, the ratcheting mechanism comprising a pawl and a plurality of teeth. The inner member comprises a pawl of the ratcheting mechanism and the outer tubular member comprises teeth of the ratcheting mechanism, the inner member and outer tubular member being disposed in relation to each other so that the pawl engages the teeth to permit rotation of the inner member in the first direction while preventing rotation in the second direction. In another aspect, the outer tubular member comprises a plurality of ratchet apertures that function as ratchet teeth and the inner member has a plurality of flexible pawls biased outwardly and at an angle to engage the ratchet apertures of the outer tubular member permitting relative rotation of the inner member within the outer tubular member in a first direction while preventing relative rotation in the second direction.

In further aspects, the flexible pawls comprise an angle at their top surfaces permitting axial movement of the inner member in relation to the outer tubular member such that the flexible pawls may be withdrawn from the ratchet apertures of the outer tubular member so that rotation in the second direction is permitted. The knotless suture anchor further comprises a spring disposed in contact with the inner member and the outer tubular member configured to bias the flexible pawls into position in the ratchet apertures of the outer tubular member. The spring is disposed such that the inner member may be moved an axially controlled amount such that the ratchet mechanism can be temporarily disengaged to permit counter-rotation of the inner member to loosen the suture.

In yet further additional aspects, the inner member comprises teeth of the ratcheting mechanism and the outer tubular member comprises a pawl of the ratcheting mechanism, the inner member and outer tubular member being disposed in relation to each other so that the pawl engages the teeth to permit rotation of the inner member in the first direction while preventing rotation in the second direction.

In other more detailed aspects, the outer tubular member comprises first and second suture thread guides disposed at the outer wall of the outer tubular member between the distal and proximal ends, the first and second suture thread guides being angularly separated from each other about the outer wall of the outer tubular member and each having a hole with a size that is large enough to receive a suture thread, the guide holes having a longitudinal axis that is substantially parallel to a longitudinal axis of the inner tubular member, wherein the thread guides do not extend beyond either the distal or proximal ends of the outer tubular member. In a further aspect, the first and second suture thread guides are disposed one hundred and eighty degrees (180°) apart on the outer wall of the outer tubular member. In another aspect, a tension-responsive indicator is formed on an eyelet in contact with a suture thread received by the eyelet and inner member, the indicator having a plurality of configurations that visually indicate the amount of tension on the suture thread.

Additionally, the knotless suture anchor further comprises first and second suture thread guide channels, each of which is disposed in alignment with a respective suture thread guide between the suture thread guide and an aperture in the outer surface of the outer tubular member, each guide channel comprising a relieved portion of the outer surface of the outer tubular member having a depth selected so as to receive a suture thread, whereby a suture thread disposed in the knotless suture anchor is guided by the thread guides and guide channels to positions that are away from contact with surrounding bone.

In yet other aspects, the apertures of the inner member and the outer tubular member for receiving a suture thread are formed with a diametrical orientation in relation to the inner member and outer tubular member. The outer wall of the outer tubular member comprises a retaining portion that is deformable outwardly into contact with the bone to retain the anchor in place in the bone, wherein as the suture thread is wrapped onto the inner member, the suture thread comes into contact with the retaining portion which thereby applies pressure to the wrapped suture thread to hold it in place on the inner member and the retaining portion also deforms outwardly into engagement with the bone to provide further anchor force of the suture anchor in the bone. In one aspect, the retaining portion of the outer tubular member comprises a buckling element. In another aspect, the retaining portion of the outer tubular member comprises a cantilevered element. The cantilevered element forms a barb extending radially outwardly and toward a proximal end of the outer tubular member. As the suture thread wraps onto the inner member, it comes into contact with the cantilevered element thereby forcing the cantilevered element outwardly into locking engagement with bone.

Turning now to method aspects in accordance with the invention, there is provided a method for holding soft tissue in apposition with a bone using a suture comprising implanting a rotatable shaft in the bone, engaging the soft tissue with an engaging portion of a suture thread, engaging an end of the suture thread with the rotatable shaft located in the bone, rotating the shaft in a first direction to wrap the engaged suture thread onto the shaft thereby applying tension to the suture thread to apply pressure to the soft tissue, and preventing the rotatable member from rotation in the second direction with a pawl and a plurality of teeth of a ratchet mechanism.

Other more detailed method aspects comprise applying force against the wrapped suture thread to prevent slippage of the suture thread on the rotatable shaft, disengaging the ratcheting mechanism temporarily to permit counter-rotation of the shaft to loosen the suture thread and guiding the suture thread that engages the rotatable shaft away from the bone about the hole so that ability of the suture thread to come into contact with the bone and cut the bone is restricted.

The features and advantages of the invention will be more readily understood from the following detailed description which should be read in conjunction with the accompanying drawings.

BRIEF DESCRIPTION OF THE DRAWINGS

FIG. 3 shows an assembled knotless suture anchor in accordance with aspects of the invention showing the suture traversing the anchor, the anchor having a pointed tip for facilitating impaction of the anchor in the bone, an aperture for receiving the suture or sutures, and a ratcheting mechanism located at the proximal end of the anchor in this embodiment for allowing rotation of an inner member in a first direction in relation to an outer tubular member while preventing counter-rotational movement of the inner member in a second, in this case opposite, direction in relation to an outer tubular member, the ratcheting mechanism having a pawl comprising the two ends of a pin mounted in the inner member, and the teeth of the ratchet being formed as part of the proximal edge of the outer tubular member.

FIG. 4 is a view of the assembled knotless suture anchor of FIG. 3 in which the outer tubular member has a deformable portion and a non-deformable portion showing the anchor expanded outwardly as a result of the inner member being rotated enough so that the suture has placed pressure on the deformable portion of the outer wall of the outer tubular member to cause it to protrude outwardly which increases the force of the anchor against the bone in which it is impacted thereby increasing the likelihood that the anchor will remain in place in the bone;

FIG. 7 provides an alternate embodiment of the outer tubular member in which it is formed in the shape of a plurality of concentric frusto-conical elements having lengthwise slits permitting outward deformation or hinging in response to force applied to them from the inner wrapping of suture on the inner member;

FIG. 8 presents the knotless suture anchor of FIG. 7 showing its engagement with two ends of a suture that has been threaded through a tendon for the purpose of drawing the tendon into a particular position between the anchor and the tendon;

FIGS. 14 through 16 present different embodiments of a suture platform for applying pressure to a tendon;

FIG. 17 provides an alternate embodiment of a ratchet mechanism in axial or longitudinal orientation in which cantilever elements of the inner tubular member mesh with teeth on the inner surface of the outer tubular member;

FIG. 18A provides yet another alternate embodiment of a ratchet mechanism in which a plurality of pawls formed on a cap of the inner member engage teeth of the outer tubular member;

DETAILED DESCRIPTION OF THE PREFERRED EMBODIMENTS

Figure 1:
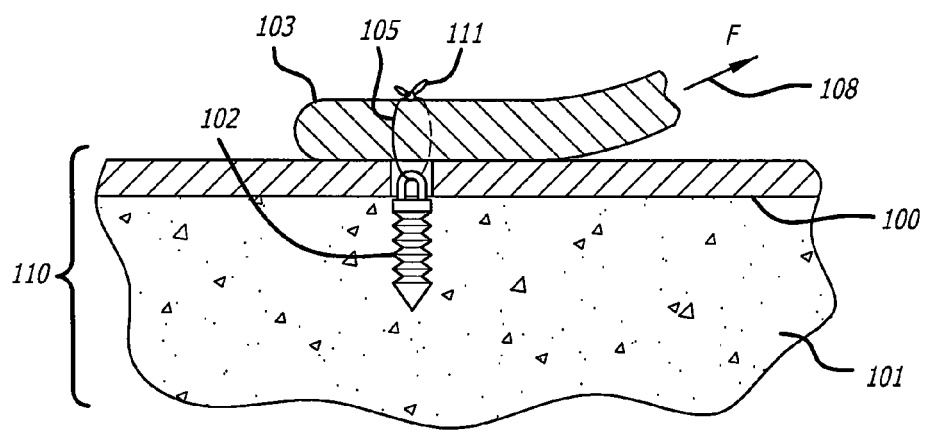
FIG. 1 depicts a prior-art technique in which a suture is placed around or through a tendon that is to be held in apposition with a humeral bone in this embodiment, the suture being located through an anchor that has been impacted or screwed in the bone and is knotted above the tendon thus resulting in a compliant configuration, the figure also showing a lateral force F that may be applied to the tendon, possibly due to patient activities.

Referring now in more detail to the exemplary drawings for purposes of illustrating embodiments of the invention, wherein like reference numerals designate corresponding or like elements among the several views, FIG. 3 shows an assembled knotless suture anchor 120 in accordance with aspects of the invention. The anchor has received an unknotted suture thread 122 and the untied ends 124 and 126 of the thread are shown at the left of the anchor. The anchor has a pointed tip 128 for facilitating penetration of the anchor into the bone with impaction, an aperture 130 for receiving the suture, and a ratcheting mechanism 132 located at the proximal end 138 of the anchor, in this embodiment, for allowing rotation of an inner member 134 in a first direction in relation to an outer tubular member 136 while preventing rotational movement of the inner member in a second, in this case opposite, direction in relation to an outer tubular member.

In FIG. 4, the anchor 120 of FIG. 3 is shown in an expanded configuration. The outer tubular member 136, also referred to herein as a shell, has a deformable portion 140 and a non-deformable portion 142, although in this case, there are two non-deformable portions. The deformable portion of the outer tubular member is shown expanded outwardly as a result of the inner member 134 being rotated enough so that the suture 122 threaded in the anchor 120 has placed outward pressure on the deformable portion of the outer wall 144 of the outer tubular member to cause it to protrude 146 outwardly which increases the force of the anchor against a hole in the bone in which it is impacted thereby increasing the likelihood that the anchor will remain in place in the bone. In this case, the outer tubular member has a plurality of longitudinal or lengthwise slits 156 spaced closely enough together to form a plurality of strips 158 of the outer surface of the outer tubular member that bow outwardly when pressure is applied to them internally by the inner member 134 and wrapped suture thread, as will be shown and described below. These strips may be considered to be buckling elements since they bow or buckle in response to radial force from the inner member. The short cantilevered elements 135 that also protrude outward may be considered to be barbs that may increase friction with and may pierce the bone to prevent movement of the anchor out of the bone.

FIGS. 3 and 4 also show a portion of the ratchet mechanism 132 used in this embodiment. A pin 148 having protruding ends (shown in more detail in later figures) engages teeth 150 that are formed in the proximal edge of the outer tubular member 136. This permits rotation of the inner member 134 in relation to the outer tubular member in a first direction but prevents counter-rotation (rotation in the opposite direction). The distal end 152 of the outer tubular member includes a spring 154, in this case a leaf spring, that is engaged in contact with both the inner member and the outer tubular member to bias the outer tubular member towards the pin 148 of the ratchet mechanism.

Figure 5A:
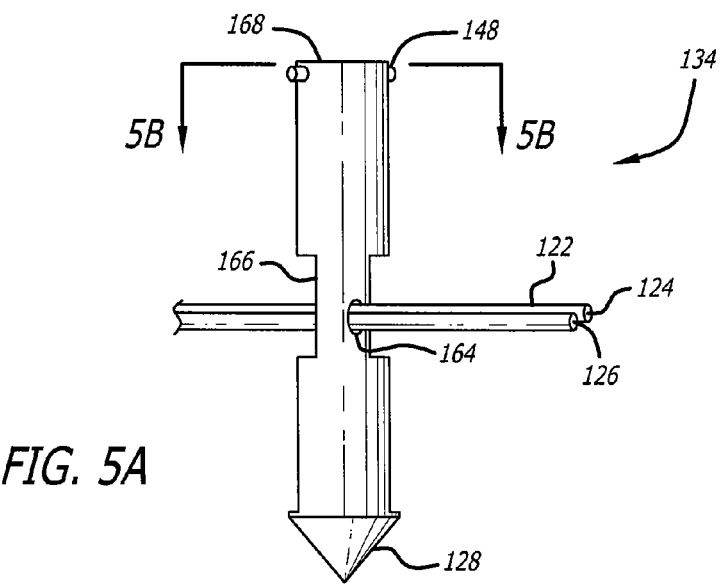
FIG. 5A shows a side view of an inner member usable in FIGS. 3 and 4 in which the member includes the pointed tip for impaction into the bone; the pawl of the ratchet mechanism formed by a pin at its proximal end, the ends of which extend outwardly to engage ratchet teeth formed in the outer tubular member, an aperture for receiving suture ends, and a reduced diameter section used for wrapping a certain length of suture before expanding the outer wall surface of the outer tubular member as shown in FIG. 4.
Figure 5B:
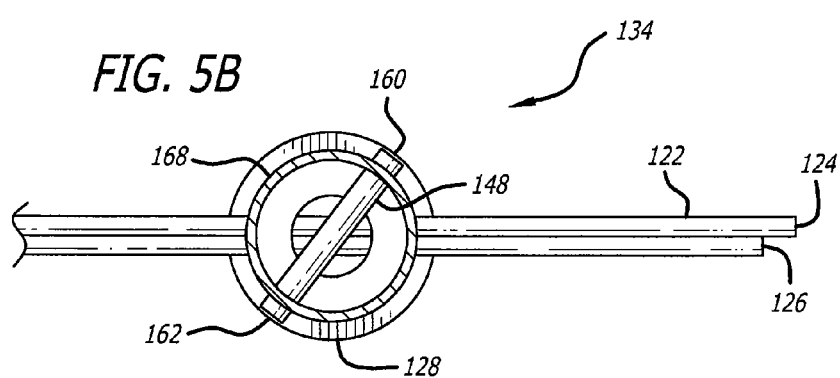
FIG. 5B is a top or proximal end-on view of the inner member of FIG. 5A showing the ratchet pawl formed by the ends of a pin in this case, the pawl doubling as a rotation control device in this embodiment to which a rotation tool may be engaged and when rotated, the pin will cause rotation of the inner member.

FIGS. 5A and 5B show a side view and top view respectively of an inner member 134, which is tubular in this case, also referred to as a rotatable shaft. This inner member is usable in FIGS. 3 and 4 and includes the pointed tip 128 for impaction into the bone at its distal end. At the proximal end 168, the inner member includes the pawl 148 of the ratchet mechanism formed by a pin 148 mounted in a diametrical orientation to the inner member and outer tubular member, the ends 160 and 162 of the pin extending outwardly to engage ratchet teeth formed in the outer tubular member as shown in FIGS. 3 and 4. The inner member has an aperture 164 for receiving the two ends 124 and 126 of the suture 122, and a reduced diameter section 166 used for wrapping the suture onto the inner member. It will be noted that the pin 148 extends across the proximal end 168 of the inner member which is hollow. This configuration enables use of a mounting tool and/or a rotation tool to engage the pin. In the case of a rotation tool engaged with the pin, rotation of the pin will cause rotation of the inner member.

Although FIG. 5B shows the inner member as being hollow through to the pointed tip 128, this need not be the case. In other embodiments the inner tubular member may be partially solid or completely solid. The designations "tubular" or "shaft" are used for convenience of reference only.

Figure 5C:
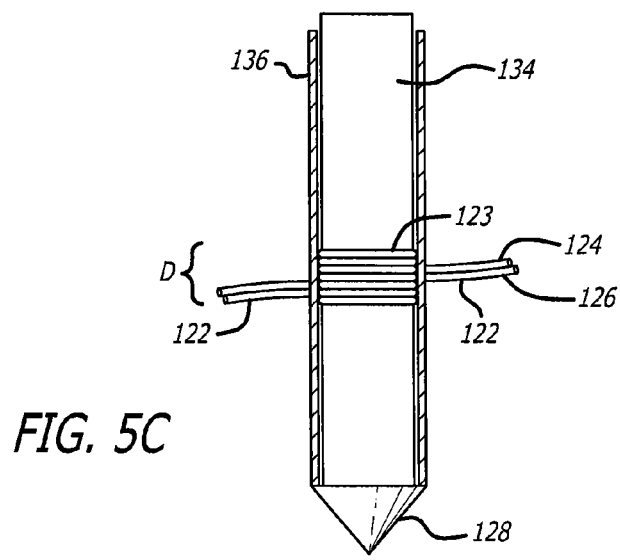
FIG. 5C is a schematic partially perspective view of the inner member with suture thread wrapped onto a portion of the inner member due to rotation of the inner member, the wrapped suture forming an enlarged outer diameter D and coming into contact with the inner wall of the outer tubular member which exerts force against the wrapped suture tending to maintain it in position on the inner member.

Turning now to FIG. 5C, the inner member 134 mounted within the outer tubular member 136 is shown in a schematic view with certain details removed for clarity of illustration. The suture thread has been wrapped 123 onto the inner member thereby forming an increased diameter D of material on the inner member. The suture is not tied or knotted and need not be knotted. The suture ends 124 and 126 are loose, however, the anchor with the configuration shown, fully captures the suture thread and provides a firm anchor of it to bone. There is no need to tie the ends of the suture thread into a knot. The diameter of suture over the inner member has increased the effective diameter of the inner member to a size where the suture has contacted the deformable portion of the outer tubular member. This contact causes the outer tubular member to apply force or pressure to the contacting suture thread which causes the suture thread to maintain its position on the inner member and to not slip or pull out of the inner member.

Figure 5D:
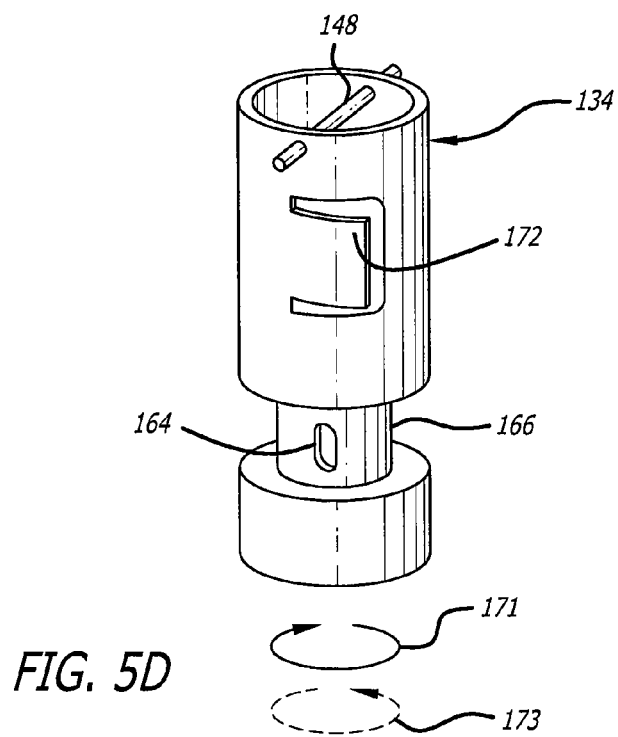
FIG. 5D presents another embodiment of the inner member in which a ratchet pawl is formed of an outwardly bent portion of the wall surface of the inner member for engaging teeth formed on the inner surface of the outer tubular member or apertures formed in the outer tubular member that function as teeth of a ratchet, the pin at the proximal end of the inner member functioning as a rotation control device for accepting a rotation tool that may be used to rotate the inner member as needed to adequately tighten a suture or sutures engaged with the inner tubular member, FIG. 5D showing the inner member as being tubular in configuration, at least in part.
Figure 5E:
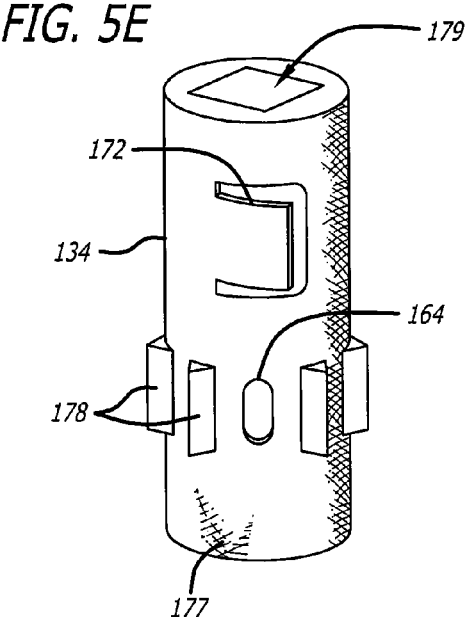
FIG. 5E shows the inner member of 5D with surface texture for increased friction with the outer tubular member and suture engaging teeth formed and positioned to engage the wrapped suture to tend to hold it in position on the inner member so that the suture will not slip out of position due to external forces applied to it.
Figure 5F:
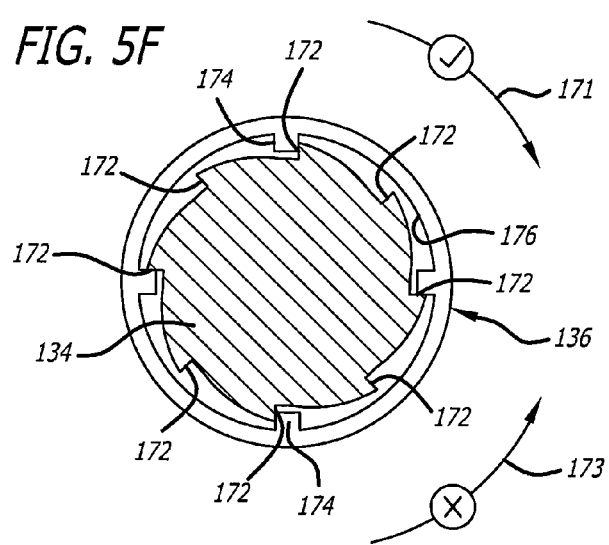
FIG. 5F shows a schematic diagram of another ratchet mechanism which is longitudinal in orientation with a plurality of pawls formed on the outer surface of the inner member to mesh with a plurality of teeth formed on the inner surface of the outer tubular member.

FIGS. 5D, 5E, and 5F present an alternate embodiment of a ratchet mechanism used to permit relative rotational motion between the inner member and the outer tubular member in one direction 171 (FIG. 5F—arrow with a check mark) and prevent counter-rotation 173 (FIG. 5F—arrow with an "X"). FIG. 5D shows an inner member 134 with the pointed tip of FIG. 5A excluded, in which a ratchet pawl is provided by means of an outwardly angled portion 172 formed from the wall of the inner tubular member. The angled portion extends outwardly far enough to engage raised teeth 174 formed on the inner surface 176 of the outer tubular member 136 as shown in the schematic view of FIG. 5F. Only one pawl 172 is shown in FIG. 5D; however, as shown in FIG. 5F, a plurality may be formed on the inner member. The raised teeth 174 on the inner surface of the outer tubular member may take forms of protrusion different from that shown in FIG. 5F. Although not shown, relief slits or other features may be formed in the outer tubular member at appropriate locations to permit its accommodation of the interference of the protrusions with the pawls 172 as they encounter each other during rotation. Also shown in FIG. 5D is the pin 148 at the proximal end of the inner member, and the aperture 164 formed in the reduced-diameter section 166.

FIG. 5E presents further detail. The outer surface of the inner member 134 includes further features in this embodiment, such as texturing 177 to assist in creating friction between the inner member and the suture threads or the outer member so that undesirable rotation or suture shift do not occur. Furthermore, suture teeth 178 may be formed on the inner member around the suture aperture 164 so that further pressure is applied to the suture thread to maintain it is position on the inner member of the anchor so that it does not slip or pull out entirely. The effect of the suture teeth 178 will be seen more clearly by reference to FIG. 11C. Additionally, a square drive socket 179 may be used for rotation of the inner member 134, or other embodiments may be provided in which other shapes or types of drivers are used, such as a hex drive.

Figure 6A:
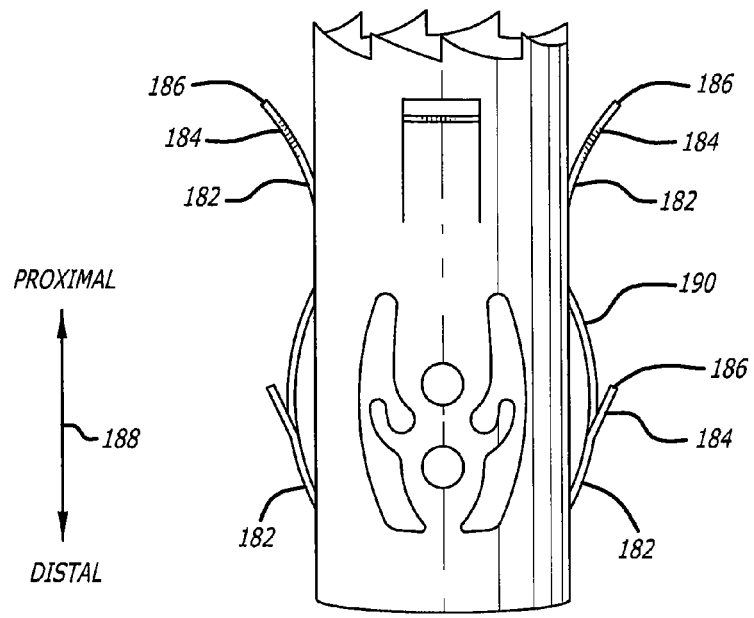
FIG. 6A shows an embodiment of the outer surface of an outer tubular member in which various portions are bent outwardly and are used to engage the walls of a bone to retain the anchor in the bone against force tending to pull it out.
Figure 6B:
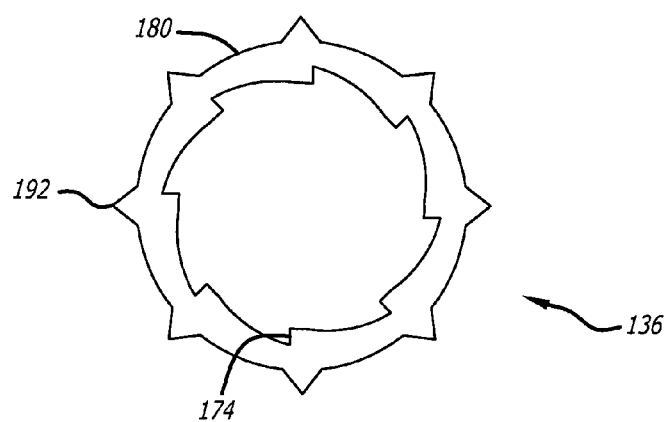
FIG. 6B shows a configuration of the outer tubular member with raised ridges in longitudinal orientation to prevent rotation of the outer tubular member in bone.

FIGS. 6A and 6B provide views of different outer surfaces 180 that may be incorporated into an outer tubular member 136 to retain the anchor both axially and rotationally in position in bone. In FIG. 6A, axial retaining devices are provided comprising various portions 182 of the outer surface 180 that are bent or are bendable outwardly for use in axially retaining the anchor in place. These axial retaining devices will engage the wall of a bone in which the anchor is impacted to retain the anchor in the bone. The protruding portions 182 in FIG. 6A include cantilevers 184 with the unattached ends 186 of the cantilevers pointing in the proximal direction 188 so that they will engage the bone to prevent its extraction if a pulling-out force is applied to the anchor. These cantilever ends may just apply frictional forces with the bone or may pierce the bone thereby generating mechanical interference with extraction. The non-cantilever portions 190 bow outwardly and are capable of applying frictional forces with the bone to resist extraction of the anchor. The outwardly bowing configuration may be caused by the expansion of the outer tubular member or some or all of the retaining members of FIG. 6A may be initially formed or pre-bent in the outwardly protruding configuration and used to engage the wall of the bone whether or not the outer tubular member is expanded.

Turning now to the top view shown in FIG. 6B, rotational retaining members 192 are formed on the outer surface 180 of the outer tubular member 136. In this case, the rotational retaining devices comprise raised ridges or teeth that extend for some longitudinal distance along the outer tubular member. During impaction, the rotational retaining devices will engage bone structure and will prevent rotation of the outer tubular member. This can be quite useful in holding the outer member stationary thereby maintaining the successful operation of the ratcheting mechanism shown, for example, in FIGS. 3 and 4. For clarity of illustration, certain drawing numerals, such as 174 and 192, are only shown with lead lines to one or a few of the elements described for that numeral. However, the numerals are meant to apply to all such relevant elements.

FIG. 7 is a side view of an alternate embodiment of an anchor 198 and an outer tubular member 200. The body of the outer tubular member is formed in the shape of a plurality of interconnected, concentric, frusto-conical elements 202, some of which include lengthwise slits 204 that permit outward expansion of their larger-diameter ends 206 in response to outward force applied to them from the wrapping of suture on the inner member 134 (FIG. 5C). For clarity of illustration, certain drawing numerals, such as 202, 204, and 206, are only shown with lead lines to one or a few of the elements described for that numeral. However, the numerals are meant to apply to all such relevant elements.

FIG. 8 presents a knotless suture anchor 198 incorporating elements of FIG. 7 showing its engagement with two ends 124 and 126 of a suture thread 122 that has been threaded through a tendon 103. The anchor may be used to adjust the tension on the suture thread and/or may be used in drawing the tendon into a desired position between the anchor and the tendon. Due to the unique design of the anchor 198 in accordance with aspects of the invention, there is no need to knot the suture thread. The combination of a ratchet mechanism 132 and internal pressure from the outer tubular member 200 on the suture thread that has been wrapped on the inner member 134, as shown and described in FIG. 5C, avoids slippage of the suture thread in the anchor. Additionally, the automatic outward expansion of the outer tubular member serves to further retain the anchor in the bone.

The suture apertures 130 in the outer tubular member 200 shown in FIGS. 7 through 10, are diametrical in orientation, and there are two of them. Having two apertures is shown as an alternative embodiment in that a single aperture may suffice.

Figure 9:
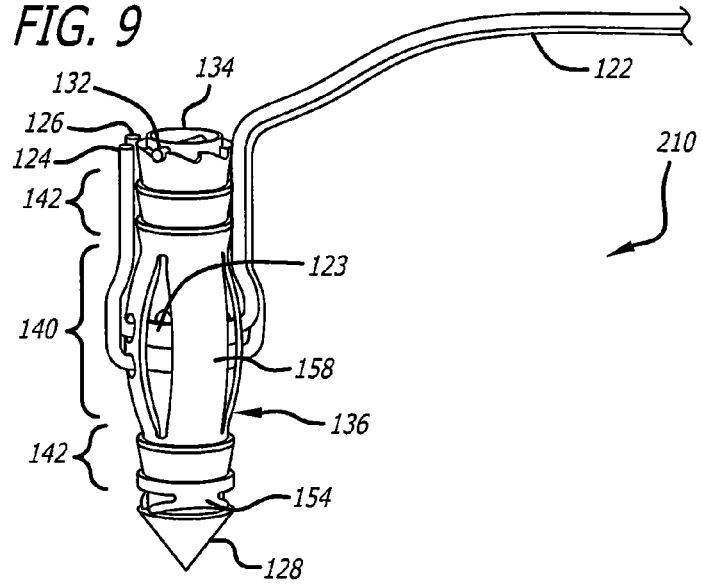
FIG. 9 is another embodiment of a knotless suture anchor in accordance with aspects of the present invention in which the body of the outer tubular member includes multiple longitudinal or axial direction slits that permit the slitted portion of the body to expand outwardly into contact with the bone hole to apply force to the wall of the bone hole to hold the anchor in place.

FIG. 9 is another embodiment of a knotless suture anchor 210 in accordance with aspects of the present invention in which the deformable portion 140 of the outer tubular member located between two non-deformable portions 142 comprises longitudinal strips 158 of the outer tubular member that bow outwardly as shown to contact surrounding bone and provide axial retention of the anchor in the bone. As the suture thread wraps 123 onto the inner member 134, the wrapped suture provides outward force against the deformable section 140 of the outer tubular member causing it to bow outwardly, while at the same time, the outer tubular member in turn provides force against the wrapping suture thread tending to prevent slippage of the suture thread on the inner tubular member.

Figure 10:
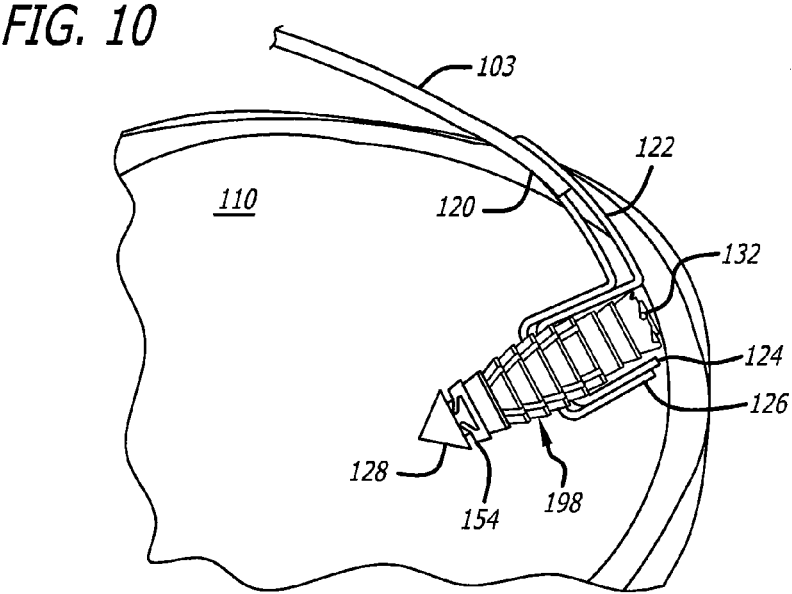
FIG. 10 is a view of the knotless suture anchor of FIGS. 7 and 8 in position in the humeral bone and being engaged with a suture that is threaded through a rotator cuff tendon to draw the tendon into desired apposition with the humeral bone and hold it in position on the humeral bone for reattachment, the anchor thus simplifying the attachment of suture to bone by eliminating the need for knots, and allowing for adjustability of the tension in the suture with a simple rotation of the inner shaft.

FIG. 10 is a view of the knotless suture anchor 198 of FIGS. 7 and 8 impacted in position in the humeral bone 110 and being engaged with a suture thread 122 that is threaded through a rotator cuff tendon 103 to draw the tendon into desired apposition 120 with the humeral bone and hold it in position on the humeral bone for reattachment. As shown, an anchor in accordance with aspects of the invention is knotless thereby simplifying the attachment of suture to bone by eliminating the need for knots, and allowing for adjustability of the tension in the suture with a simple rotation of the inner shaft.

Figure 11A:
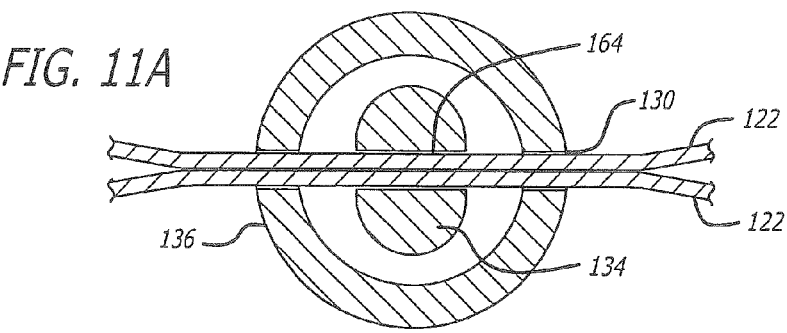
FIG. 11A is a schematic view showing the inner rotatable shaft with a suture thread located through it.
Figure 11B:
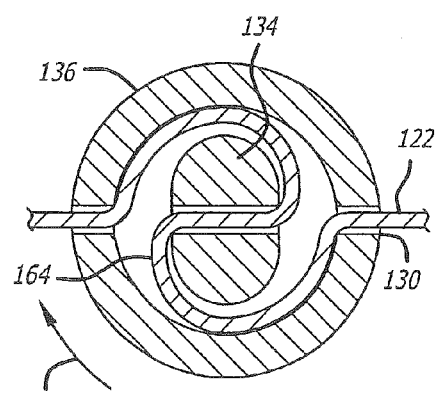
FIG. 11B is an axial view of the inner member being assembled with the outer tubular member with a suture end received by the aperture of the inner member and the inner member then rotated by 180° resulting in a tortuous path of the suture creating greater friction between the suture and the inner member to lessen the possibility of slippage of the suture in the inner rotating member, the inner member having a solid portion in this embodiment which may be located as shown in the reduced-diameter length of FIG. 5A.
Figure 11C:
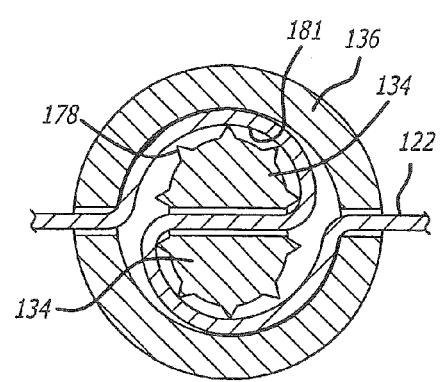
FIG. 11C is a view of another embodiment of an inner member in which protruding teeth are formed to further engage the threaded suture to provide even more force against it to maintain it in position in the outer tubular member, the clearance between the teeth and the outer tubular member having been reduced to further provide force against the suture to maintain it in position.

FIGS. 11A through 11C are axial cross-section views of the inner member 134 being assembled with the outer tubular member 136 and the path of the suture thread 122 threaded through the aperture 164 of the inner member and the aperture 130 of the outer tubular member. In FIG. 11A, the suture comprises two threads. The aperture of the inner member is aligned with the aperture of the outer tubular member and the suture threads 122 are placed straight through the anchor. For clarity of illustration, FIGS. 11B and 11C only show a single suture thread. In FIG. 11B, the inner member has been rotated by one hundred and eighty degrees (180°) showing how the suture thread is wrapped about the inner member 134. This increasing wrapping will increase the force of the suture thread on the inner tubular member thereby lessening the possibility of slippage of the suture in the inner tubular member.

FIG. 11C provides an alternate embodiment of the inner member in which it includes suture teeth 178 as shown in FIG. 5E. These suture teeth are used to assist in maintaining the suture thread 122 in position on the inner member 134. Also, in this embodiment, there is less clearance between the inner member and the inner wall 181 of the outer member, thus putting further pressure or force on the suture thread 122 to maintain its position on the inner member.

Figure 12A:
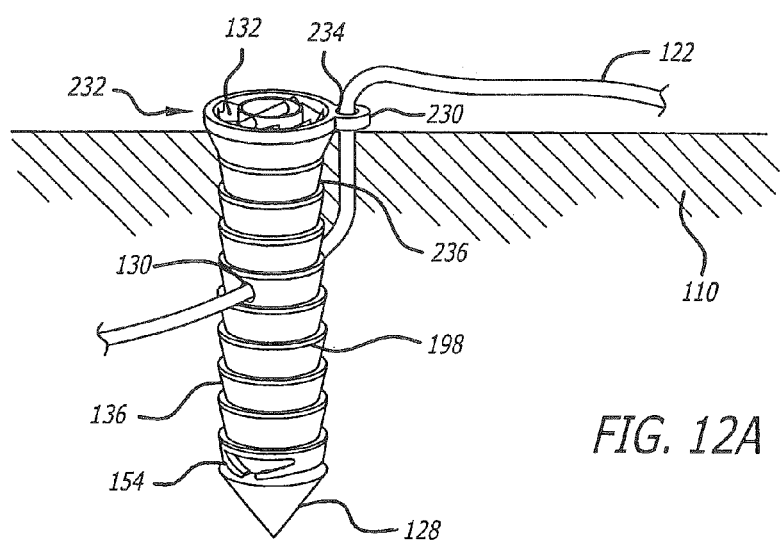
FIG. 12A shows the knotless suture anchor of FIGS. 7 and 8 with the addition of an eyelet used for guiding the suture along the outer surface of the outer tubular member to control contact of the suture with the bone, the eyelet located at the proximal end of the anchor above the bone in this embodiment

FIG. 12A provides a view of the anchor 198 of FIGS. 7 and 8 impacted into bone 110 showing the addition of a suture thread guide 230 disposed at the proximal end 232 of the outer tubular member 136. In this embodiment, the suture thread guide comprises an eyelet, the aperture 234 of which receives a suture thread to guide the suture thread along the outer surface 236 of the outer tubular member thereby restricting contact of the suture with the surrounding bone 110. It has been noted that if not so guided or restricted in movement, the suture thread 122 can have a sawing or "cheese cutting" effect on the bone 110 when forces are imparted to it that cause the suture to move, thereby undesirably removing some of the bone. Such sawing or bone cutting can undesirably loosen the tension on the suture since the path of the suture will have now been shortened.

Another advantage to the eyelet is that it redirects the force that the suture tension applies to the anchor. When not confined by the eyelet, the suture can apply outwardly-directed force on the anchor that tends to force the anchor out of its position in the bone. When an eyelet is used however, that eyelet functions to translate the tension on the suture to lateral force on the anchor thereby greatly lessening the tendency of the suture tension to force the anchor from the bone and thereby providing a more stable anchor.

Figure 12B:
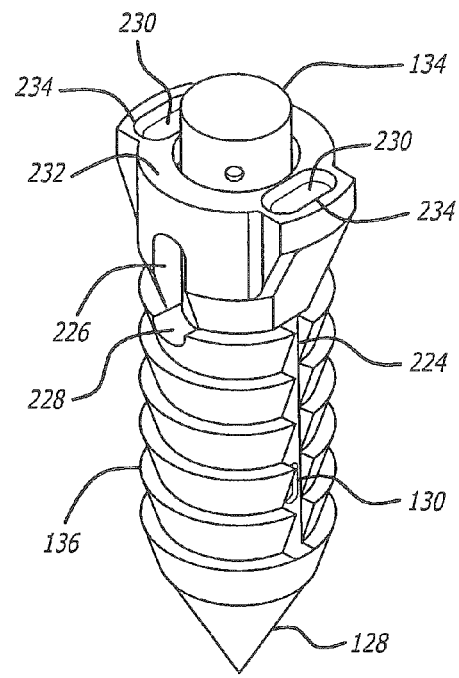
FIG. 12B presents another embodiment having two eyelets, both of which are located at the proximal end of the outer tubular member and do not extend beyond that proximal end, an internal ratchet mechanism in which apertures in the outer tubular member function as teeth and a pawl or pawls are formed on the rotatable inner member to engage the ratchet apertures, and also showing suture thread channels formed longitudinally in the outer surface of the outer tubular member in which suture thread may be positioned.

FIG. 12B presents another of the preferred embodiments in which two suture thread guides 230 are provided. The apertures 234 of the guides are oriented in parallel with the longitudinal axis of the inner member 134 and are located at the proximal end 232 of the outer tubular member 136. As shown, the suture thread guides do not extend beyond the proximal end of the outer member. Aligned with each of the thread guides 230 in this embodiment is a guide channel 224 located between the guide 230 and the aperture 130 in the outer member. Only one guide channel can be seen in FIG. 12B. Each guide channel comprises a relieved portion of the outer surface of the outer tubular member having a depth selected so as to receive a suture thread or threads, whereby a suture thread disposed in the knotless suture anchor 218 is guided by the thread guides and guide channels to positions that are away from contact with surrounding bone 110.

Portions of a ratcheting mechanism can also be seen in FIG. 12B. In this case, the ratchet teeth are provided by ratchet apertures 226, one of which can be seen. Shown as engaged with this ratchet aperture is a flexible ratchet pawl 228 that is mounted on and rotates with the inner member 134, although internal details cannot be seen in this figure. Refer to FIG. 5D for a possible flexible pawl that would function in the embodiment of FIG. 12B. A plurality of pawls may be used on the inner member. A plurality of ratchet apertures may also be provided.

Figure 12C:
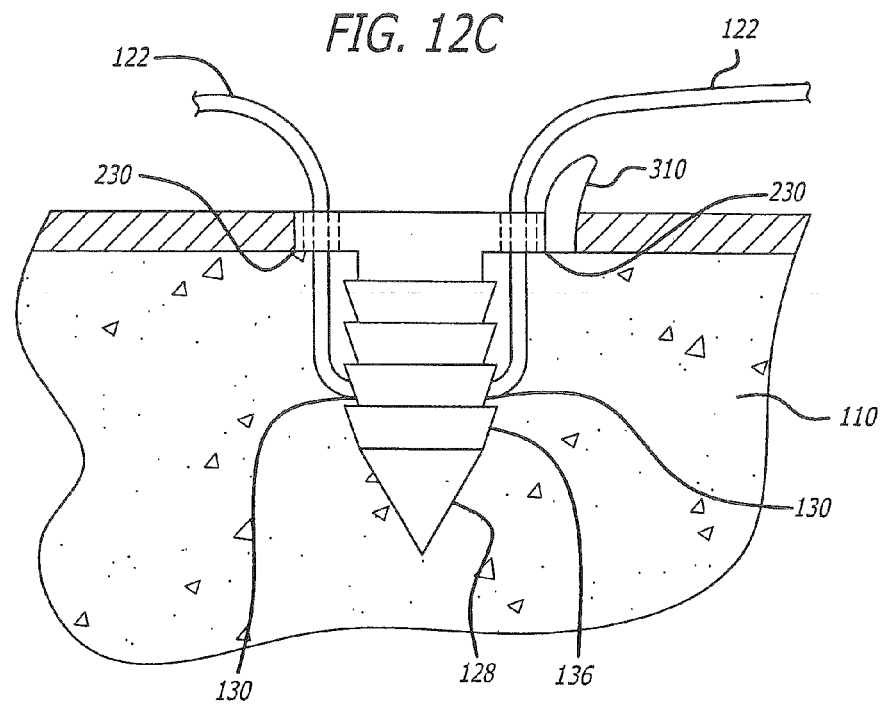
FIG. 12C presents a view of an anchor mounted in bone, the anchor having an eyelet with a suture tension indicator, which in this view is oriented longitudinally thereby indicating minimum tension on the suture.
Figure 12D:
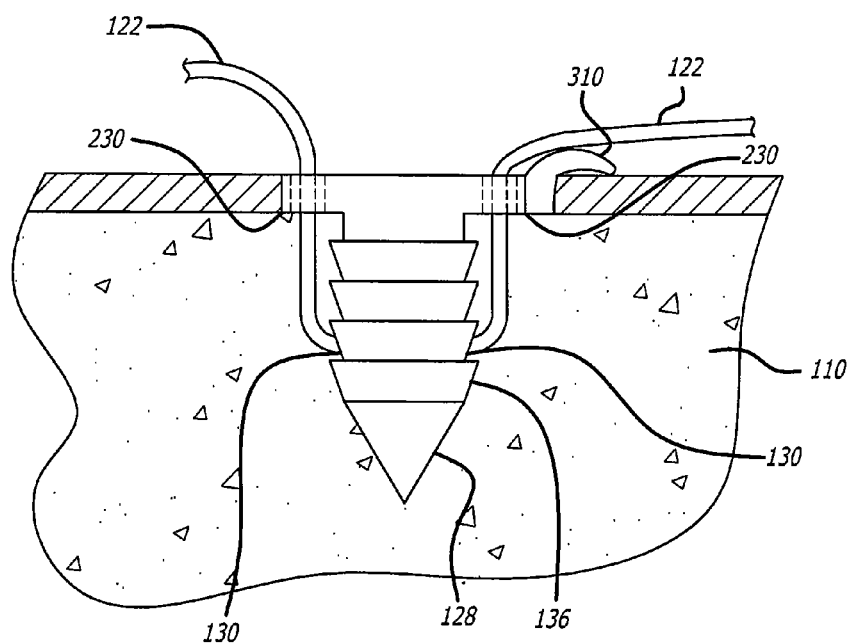
FIG. 12D shows the tension indicator of FIG. 12C but in this case, bent into a radially outward configuration due to contact with the suture under tension, thereby indicating that the suture is at the maximum safe level of tension, in this embodiment.

A further eyelet-connected feature is shown in FIGS. 12C and 12D. A tension indicator 310 is formed in this embodiment at the outer edge of one of the eyelets 230, also know as a suture guide. The tension indicator is located such that it will contact a suture thread 122 received by the guide 230 and will give a visual indication of the tension on that thread 122. In this case shown in FIG. 12C, the indicator 310 has been formed in a longitudinal configuration parallel with the longitudinal axis of the anchor and remains in that configuration when there is no tension on an engaged suture thread. However, the indicator is meant to deform due to tension on the suture and when that tension is high, it will deform to the configuration shown in FIG. 12D. The indicator 310 in FIG. 12D is no longer longitudinally oriented but is instead now radially or diametrically oriented providing a highly visual indication of the much higher suture tension level. In one embodiment, the mounting and resistance to deformation of the indicator 310 were selected such that the indicator would assume the configuration shown in FIG. 12D only when the tension on the suture was at the highest level that the suture thread is capable of handling safely. Above that level of tension, the suture thread is in danger of breaking.

Thus the tension indicator of FIGS. 12C and 12D provides a highly visual indication of the level of tension. The shape of the indicator may be varied as desired however, it must come into contact with the engaged suture thread.

Figure 13:
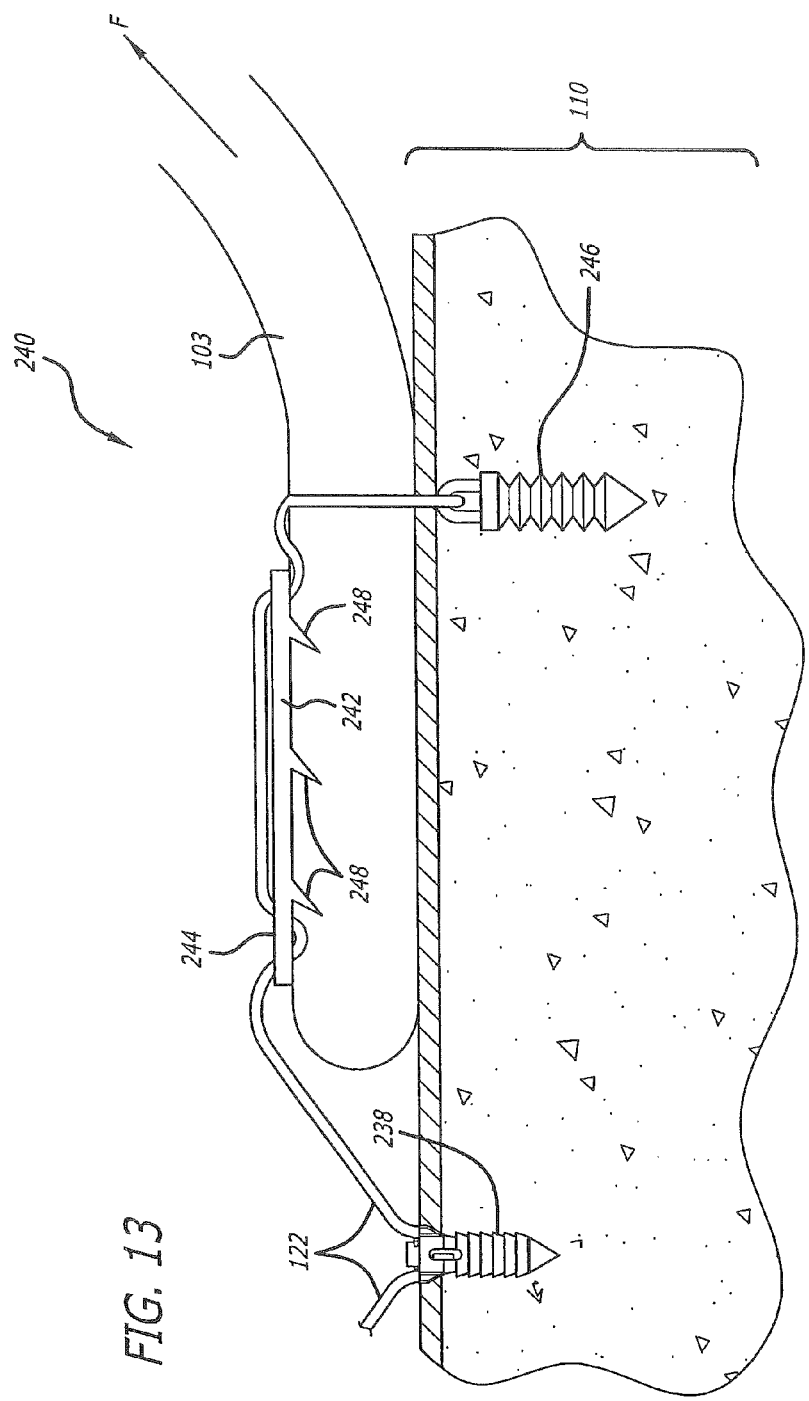
FIG. 13 is a view of a system comprising two or more anchors with a suture platform functioning with sutures to create a suture bridge that increases the surface area of the suture force against the tendon to force it downward into greater contact with the bone, the suture bridge in this embodiment having the suture platform that has a surface area that exceeds that of a suture and which may be straight or curved depending on the application in which it is to be used, and further comprising in this embodiment angled spikes to engage the tendon and provide greater control over it to oppose any lateral force F that may be applied to the tendon that would tend to move the tendon and create a position gap as demonstrated in FIG. 2.

FIG. 13 is a view of a tendon repair system 240 comprising two or more anchors with a suture platform 242 functioning with a suture 122 or sutures to create a suture bridge 244 that increases the surface area of the suture 122 force against the tendon 103 to force the tendon downward into greater, and more uniform, apposition with the bone 110 for reattachment and healing. The suture bridge in this embodiment comprises the suture platform that has a surface area that exceeds that of a suture. Two anchors are shown, one of which may be a standard passive or static anchor 246 that is impacted into the bone and that simply includes a loop for receiving a suture thread. The other anchor may be a knotless anchor 238 such as one in accordance with the present invention. A suture thread may be looped through the passive anchor, then drawn through the tendon and into the suture platform as shown, and either through or around the tendon again, and the loose ends of the suture thread received by the knotless anchor 238. The inner tubular member of the knotless anchor is then rotated to tighten the suture thread onto the suture bridge thereby pressing the tendon into better contact with the bone.

Figure 2:
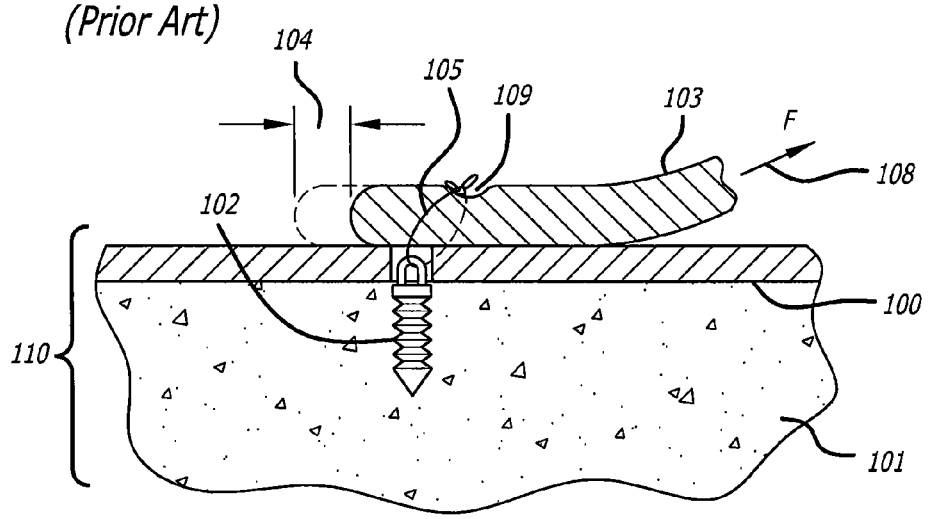
FIG. 2 demonstrates the formation of a gap in the position of the tendon in relation to the position of the tendon in FIG. 1; the movement of the tendon in forming this gap negatively affecting the reattachment and healing of the tendon with the bone, the gap formation being caused by the application of a level of the lateral force F to the tendon that overcomes the suture downward force causing the tendon to move from its desired healing position, as shown in FIG. 1.

The suture platform 242 may have spikes 248 as shown in FIG. 13 that enter the tendon to provide better control over the position of the tendon and to keep it in the desired fixed position in apposition with the bone. When the spikes are angled as shown in FIG. 13, in a direction against the expected force to which the tendon would be subjected, the tendon is less likely to move and create positions gaps as shown in FIG. 2. In one embodiment, the spikes should be short enough so that they do not completely traverse the tendon and make contact with the bone. That is, the length of the spikes should be shorter than the width of the tendon with which they are engaged.

The suture platform 242 may be straight or curved or have other shapes depending on the application in which it is to be used. For example, the platform may have the shapes 250, 252, or 254 as shown in FIGS. 14, 15, and 16 respectively, depending on the tendon to be healed and the bone to which it is attached or to which it is to be reattached. All platforms may have apertures 256 and/or may have specially designed lateral suture guides 258 such as those shown in FIG. 15. The shapes and configurations shown in the figures are exemplary only. Other shapes may be conceived and built that will fall within the scope of the present invention.

Figure 18B:
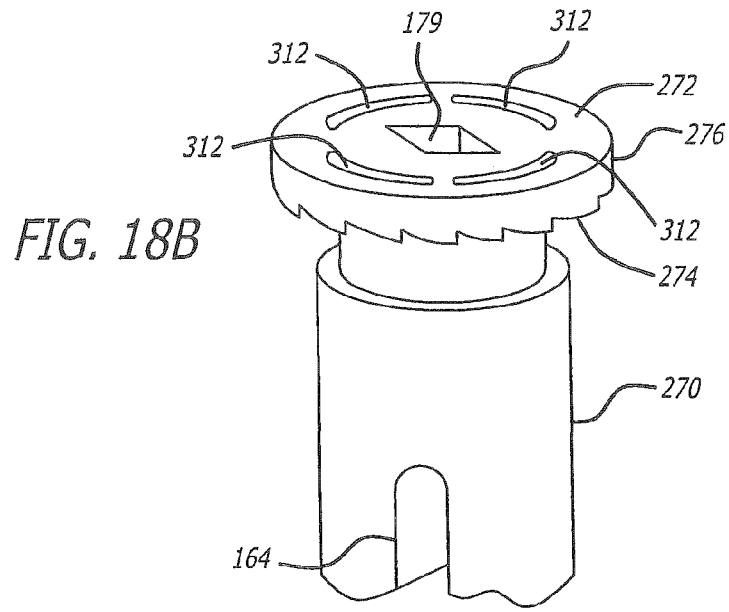
FIG. 18B provides a view of a flexible cap used as part of the ratchet mechanism, the cap having relieved portions thereby increasing its flexibility to obviate the need for a separate spring, the cap providing a spring function as well as a ratchet function.

Other ratcheting mechanisms may be used, two examples of which are shown in FIGS. 17, 18A, and 18B, although other mechanisms may function effectively. In FIG. 17, the inner member 260 has been formed with a plurality of axially-extending ratchet pawls 262. These are cantilever in nature and are flexible enough to bend inwardly as they follow the ramp 264 of the teeth 266 formed on the inside surface of the outer tubular member 136. The pawls then snap back outwardly into their normal position after passing the ramp 264 of a tooth 266 and encountering the stop surface 268 of the teeth. They will then prevent counter-rotation of the inner tubular member 260.

In FIG. 18A, the inner member 270 has a cap 272 having teeth 274 formed at its distal end 276. The outer tubular member 278 has teeth 280 formed at its distal end 282. The teeth on the inner tubular member and those on the outer tubular member are complementary and when the inner tubular member is slid into position within the outer tubular member, the meshing teeth will act as a ratchet mechanism. A spring, such as the leaf spring 154 shown in FIG. 4, is used to maintain the ratchet mechanism functioning. In the case where the outward bowing of the deformable portion 140 (FIG. 9) shortens the length of the outer tubular member, the spring 154 nevertheless will force the teeth of the outer tubular member into continued engagement with the pawl or pawls of the inner tubular member. Such an approach may not be needed when the ratchet mechanism is formed longitudinally such as in FIG. 5D.

FIG. 18B presents a top perspective view of the cap 272 of FIG. 18A. Shown on the top surface is the drive socket 179 of FIG. 5E, as well as relieved portions 312 functioning to increase the flexibility of the outer perimeter of the cap. The size and locations of the relieved areas 312 are selected to result in a desired amount of spring in the cap such that it will function as a ratchet device wherein the perimeter rides up the ramps of the teeth 280 on the outer tubular member 278 yet will spring back into engagement with each stop surface of the ratchet at the ramp's end. Such spring function will obviate the need for a separate spring to hold the ratchet teeth and pawl together.

As used herein, "apposition" is meant to mean in contact with as well as have other meanings commonly associated with it. For example, when the tendon is in "apposition" with the bone, one meaning is that the tendon is in contact with the bone.

In another feature, depending on the particular ratchet mechanism, the inner member may be moved an axially controlled amount to disengage its pawl or pawls from the teeth of the outer tubular member such that the ratchet mechanism is temporarily disengaged. This disengagement will permit counter-rotation of the inner member in relation to the outer tubular member to loosen the suture threaded through it. In such a configuration, the spring is disposed so that it can be overcome to disengage the ratchet mechanism, yet has enough length to force the ratchet mechanism back into engagement once the separating force is removed.

Figure 19:
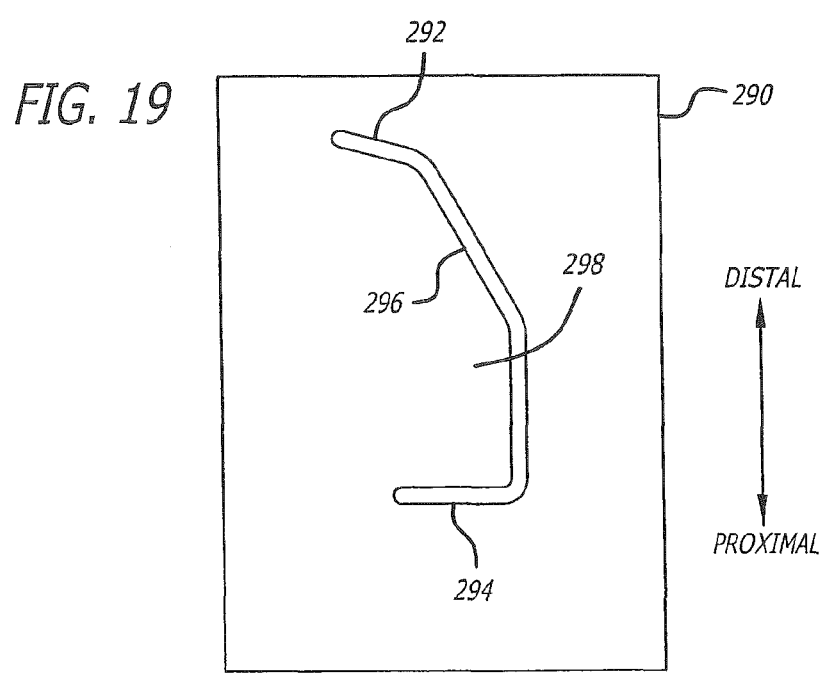
FIG. 19 shows the formation of a pawl on the inner member, the pawl having a ramp portion that may be used to dis-engage the pawl with the teeth of a ratchet mechanism to facilitate temporary disengagement and re-engagement of the ratchet mechanism.
Figure 20:
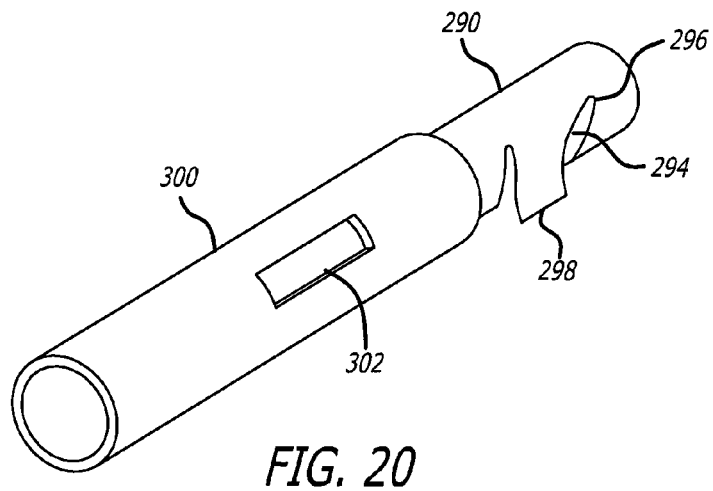
FIG. 20 shows a view of the use of the pawl of FIG. 19 with the inner member and outer tubular member, in this case the inner member being axially withdrawn from the aperture tooth of the outer member so that the ratchet mechanism is non-functional and the inner member can be rotated in either rotational direction to loosen the tension on a suture if necessary.

An embodiment of such a mechanism is shown in FIGS. 19 and 20. In FIG. 19, the inner member 290 is cut 292 as shown to create a longitudinal pawl 294 having a ramp 296 and a straight portion 298 for engaging teeth formed on the inside of the outer tubular member (see for example FIG. 5F). The pawl of FIG. 19 will look similar to that of FIG. 5D numeral 172 except that the pawl of FIG. 19 will have the ramp 296 at the distal or proximal end of the pawl. As shown in FIG. 20, the inner member 290 has been pulled axially in relation to the outer tubular member 300 so that the pawl 294 disengages from the teeth 302 (in this case a ratchet aperture functioning as a tooth) and the suture can then be loosened from the anchor as desired by rotating the inner member in a counter-rotation direction, or the rotation direction prevented by an engaged ratchet mechanism. The ramped edge 296 of the pawl facilitates this disengagement of the ratchet mechanism in that it more easily permits the pawl 294 to be separated from the aperture 302. Also, there may be an internal spring (not shown) that biases the inner member into the outer member so that the ratchet mechanism is engaged. This spring force would need to be overcome to disengage the ratchet as described above.

The inner member may then be slid back into the outer member to re-engage the ratchet mechanism for normal operation. In the case shown in FIG. 20, the inner member is shown as having been axially moved much farther than it would normally be moved for disengagement. This is shown solely for purposes of clarity in illustration. Normally, the inner member would be axially moved only far enough for the pawl 298 to disengage the ratchet aperture 302, or just out of the "tooth." It should be appreciated that the embodiment shown in FIGS. 19 and 20 is exemplary only. Other implementations may be created that will fall within the scope of the invention.

Figure 21:
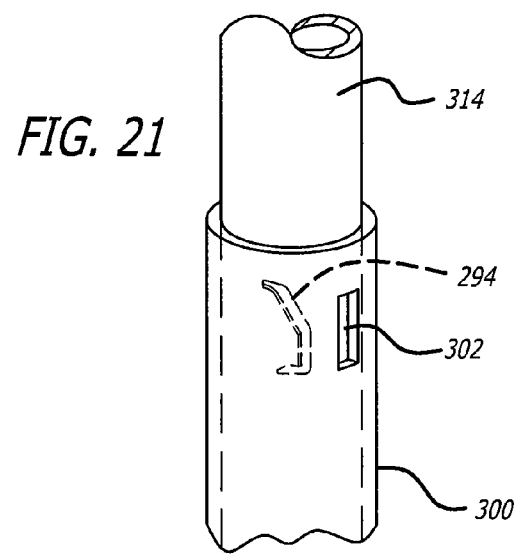
FIG. 21 provides a view of a ratchet disengagement tool for use with the configuration of FIG. 20 whereby the inner member need not be axially moved to render the ratchet mechanism non-functional.

One of those other possible implementations is shown in FIG. 21, in which a disengagement shaft 314 is used to slide between the outer tubular member 300 and the inner member (not shown) to move the pawl 294 inward away from the apertures 302 so that the inner member may be rotated in either direction. When in this configuration, the tension on the suture can be lessened. The disengagement shaft may be axially shifted between functional (disengaging the ratchet mechanism) and non-functional (not affecting the ratchet mechanism) positions.

Figure 22:
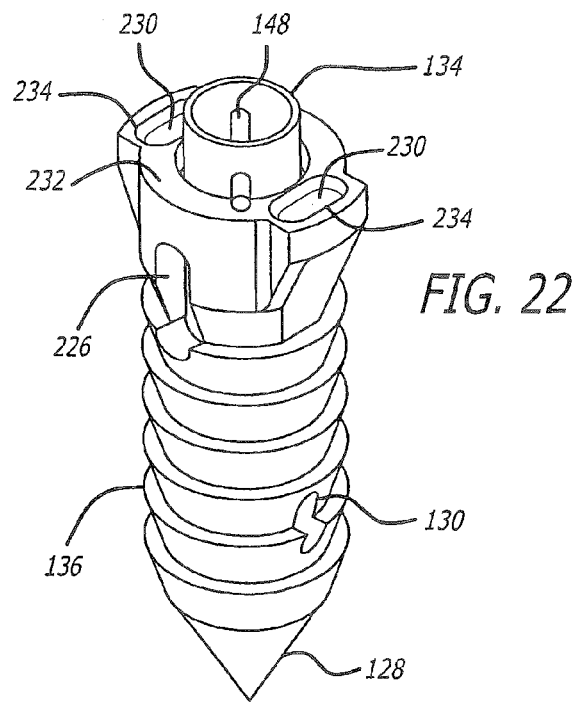
FIG. 22 provides a further embodiment of a knotless anchor in accordance with aspects of the invention in which a pin through the inner member is used as a rotation device.
Figure 23:
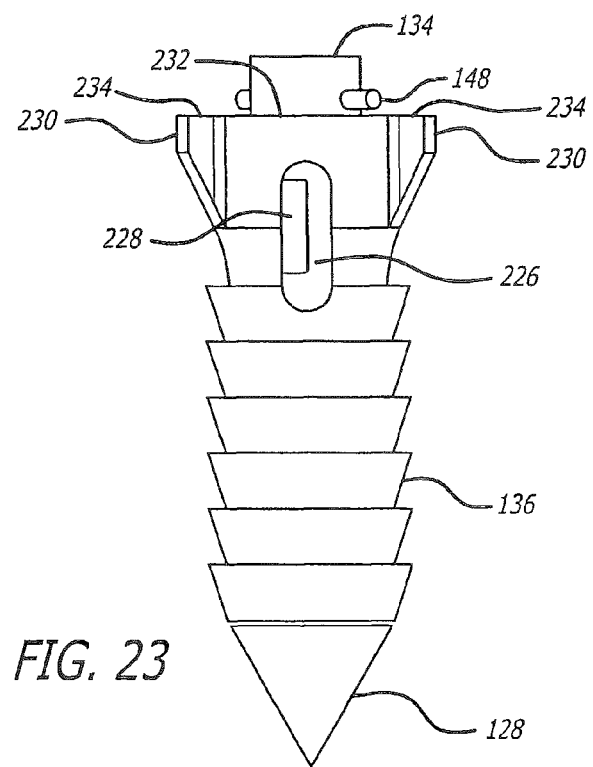
FIG. 23 is a side view of FIG. 22 showing further detail of the pawl formed on the inner member.

Referring now to FIGS. 22 and 23, there is shown a further embodiment of an anchor 320 in accordance with aspects of the invention in which an inner rotatable member 134 has a diametrical pin 148 mounted at its proximal end 232 that may be used to receive a rotating device. This embodiment has similarities to that of FIG. 12B except that no suture channels are formed in the outer surface of the outer tubular member. The internal ratcheting mechanism is provided however as well as two eyelets or suture guide devices 230 located opposite each other. As in FIG. 12B, the ratchet mechanism uses aperture teeth 226 and a pawl 228 is mounted to the inner member.

In one embodiment, anchor 120 could be made from a non-bioresorbable or non-biodegradable material such as titanium, stainless steel, nickel-titanium alloy (nitinol), PEEK or other suitable material commonly used in orthopedic implants. Polymers synthesized from monomers comprising esters, anhydrides, orthoesters, and amides are particularly suitable for biodegradation useful for an alternative embodiment anchor 120 that is bioresorbable or biodegradable. Examples of biodegradable polymers are polyglycolide, polylactide, poly-α-caprolactone, plydiaxanone, polyglyconate, polylactide-co-glycolide, and block and random copolymers of these polymers.

It may be desired to reduce the likelihood of the development of fibrotic tissue around the directional anchors or angled spikes 248 (FIG. 13) which may increase stiffness in the tendon. Certain drugs such as steroids, have been found to inhibit cell growth leading to scar tissue or fibrotic tissue growth. Examples of therapeutic drugs or pharmacologic compounds that may be loaded onto the directional anchors (angles spikes) or into a polymeric coating on the anchors or infused into the area surrounding the anchors include steroids, taxol, aspirin, prostaglandins, and the like. Various therapeutic agents such as antithrombogenic or antiproliferative drugs are used to further control scar tissue formation. Examples of therapeutic agents or drugs that are suitable for use in accordance with the present invention include 17-beta estradiol, sirolimus, everolimus, actinomycin D (ActD), taxol, paclitaxel, or derivatives and analogs thereof. Examples of agents include other antiproliferative substances as well as antineoplastic, anti-inflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, anti-inflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone. It may also be desirable to incorporate osteogenic or angiogenic factors, or growth factors such as TEFB or BMP-X with the directional anchors to promote bone to tendon healing.

Although the ratchet is shown with the pawl located on the inner member and the teeth located on the outer tubular member, other configurations of a ratchet may be equally usable, some of which have been shown and described. In another embodiment, a pawl may be located on the outer member with the ratchet teeth locate on the inner member. Other arrangements may be used to create a movement in one direction. Furthermore, the anchor is repeatedly shown as being positioned in the bone so that its proximal end is about level with the bone surface. However, the anchor may in fact be mounted so that its proximal end is further within the bone or further out of the bone. Additionally, the material used for the anchor may be selected in dependence on the hardness of the tissue in which the anchor is to be mounted. Harder tissue may require a titanium anchor while softer tissue may allow use of a softer plastic material for the anchor. The design of various embodiment enables an anchor in accordance with the invention to be directly impacted into bone.

Method claims are not limited to the order of the method steps claimed unless specifically so stated. Unless so specifically stated, the method steps may be performed in a different order and still fall within the scope of the claim.

Although the invention has been described herein with specific reference to preferred embodiments thereof, it will be appreciated by those skilled in the art that various modifications, deletions, and alterations may be made to such preferred embodiments without departing from the scope of the invention.

What is claimed is:

1. A knotless suture anchor for implanting in a bone hole, comprising:
   an outer tubular member having a distal end, a proximal end, and an outer wall having an outer dimension configured to fit and be retained within the bone hole and a retaining portion that is deformable and configured to outwardly expand into contact with a wall of the bone hole to retain the anchor within the bone hole;
   the outer tubular member having an inner wall including at least one ratcheting aperture therethrough;
   an inner member being rotatably disposed within the outer tubular member, the inner member having a wall with an outer diameter, a proximal end having a pin extending across the outer diameter and a distal end, the distal end having a pointed tip extending beyond the distal end of the outer tubular member, and at least one pawl formed from, and angled outwardly from, the wall of the inner member and engageable with the at least one ratcheting aperture, said pawl comprising a ramp portion configured to disengage the pawl from the ratcheting aperture during relative axial movement of the inner and outer members; and
   the inner member and the outer tubular member each having a suture aperture for receiving a suture thread;
   wherein the outer diameter of the inner member is selected to be large enough such that as the inner member having a suture thread received by its suture aperture is rotated, while the suture anchor is implanted in the bone hole, the suture thread is drawn through the suture aperture of the outer tubular member and wraps onto the inner member thereby increasing the effective diameter of the inner member with the wrapped suture thread coming into contact with the inner wall of the outer tubular member, such contact adapted to exert an outward force on the retaining portion of the outer tubular member to outwardly deform the retaining portion into contact with the wall of the bone hole.

2. The knotless suture anchor of claim 1, wherein the outer dimension of the outer tubular member is adapted to have a friction fit with the bone.

3. The knotless suture anchor of claim 1, wherein the outer wall of the outer tubular member includes engagement features formed thereon configured to engage the bone hole in which the anchor is positioned.

4. The knotless suture anchor of claim 1, wherein the ratcheting aperture and pawl are configured to permit rotation of the inner member in a first direction in relation to the outer tubular member while preventing rotation of the inner member in a second direction.

5. The knotless suture anchor of claim 1, wherein:
   the outer tubular member comprises a plurality of ratchet apertures that function as ratchet teeth; and
   the inner member has a plurality of flexible pawls biased outwardly and at an angle to engage the ratchet apertures of the outer tubular member permitting relative rotation of the inner member within the outer tubular member in a first direction while preventing relative rotation in the second direction.

6. The knotless suture anchor of claim 5, wherein the flexible pawls comprise the ramp portion at their top surfaces permitting axial movement of the inner member in relation to the outer tubular member such that the flexible pawls may be withdrawn from the ratchet apertures of the outer tubular member so that rotation in the second direction is permitted.

7. The knotless suture anchor of claim 5, further comprising a spring disposed in contact with the inner member and the outer tubular member configured to bias the flexible pawls into position in the ratchet apertures of the outer tubular member.

8. The knotless suture anchor of claim 7, wherein the spring is disposed such that the inner member may be moved an axially controlled amount such that the ratchet mechanism is temporialy disengaged to permit counter-rotation of the inner member to loosen the suture.

9. The knotless suture anchor of claim 4, further comprising a spring disposed in contact with the inner member to bias the inner member into a predetermined position in relation to the outer tubular member at which the ratchet aperture is engaged with the pawl to prevent rotation in the second direction.

10. The knotless suture anchor of claim 9, wherein the spring is disposed such that the inner member may be moved by a predetermined amount against the spring such that the ratchet aperture is temporarily disengaged from the pawl to permit rotation of the inner member in the second direction.

11. The knotless suture anchor of claim 1, further comprising a tension indicator located at the outer tubular member in contact with the suture, wherein the tension indicator is adapted to visually indicate an amount of tension on the suture.

12. The knotless suture anchor of claim 1, wherein the outer tubular member comprises first and second suture thread guides disposed at the outer wall of the outer tubular member between the distal and proximal ends, the first and second suture thread guides being angularly separated from each other about the outer wall of the outer tubular member and each having a hole with a size that is large enough to receive a suture thread, the guide holes having a longitudinal axis that is substantially parallel to a longitudinal axis of the inner member, wherein the thread guides do not extend beyond either the distal or proximal ends of the outer tubular member.

13. The knotless suture anchor of claim 12, wherein the first and second suture thread guides are disposed one hundred and eighty degrees (180°) apart on the outer wall of the outer tubular member.

14. The knotless suture anchor of claim 12, further comprising first and second suture thread guide channels, each of which is disposed in alignment with a respective suture thread guide between the suture thread guide and an aperture in the outer surface of the outer tubular member, each guide channel comprising a relieved portion of the outer wall of the outer tubular member having a depth selected so as to receive a suture thread, whereby a suture thread disposed in the knotless suture anchor is configured to be guided by the thread guides and guide channels to positions that are away from contact with surrounding bone.

15. The knotless suture anchor of claim 12, further comprising a tension indicator located at one of said suture thread guides in contact with the suture, wherein the tension indicator is adapted to visually indicate an amount of tension on the suture.

16. The knotless suture anchor of claim 1, wherein the suture apertures of the inner member and the outer tubular member for receiving a suture thread are formed with a diametrical orientation in relation to the inner member and outer tubular member.

17. The knotless suture anchor of claim 1, wherein
as the suture thread is wrapped onto the inner member, the suture thread comes into contact with the retaining portion which thereby applies pressure to the wrapped suture thread to hold it in place on the inner member.

18. The knotless suture anchor of claim 17, wherein the retaining portion of the outer tubular member comprises a buckling element.

19. The knotless suture anchor of claim 17, wherein the retaining portion of the outer tubular member comprises a cantilevered element.

20. The knotless suture anchor of claim 19, wherein the cantilevered element forms a barb extending radially outwardly and toward a proximal end of the outer tubular member.

21. The knotless suture anchor of claim 20, wherein as the suture thread wraps onto the inner member, it is configured to come into contact with the cantilevered element thereby forcing the cantilevered element outwardly into locking engagement with the wall of the bone hole.

22. A knotless suture anchor for implanting in a bone hole, comprising:
a rotatable shaft having an outer diameter, a proximal end having a pin extending across the outer diameter, a distal end having a pointed tip, and a diametrical suture aperture for receiving an end of a suture thread;
a shell disposed about the rotatable shaft, the shell having a length and a diametrical suture aperture through which an end of a suture thread may be passed into engagement with the rotatable shaft and a retaining portion that is configured to deform outwardly into contact with a wall of the bone hole to retain the anchor within the bone hole, the pointed tip extending beyond a distal end of the shell;
a ratchet mechanism configured to permit the rotatable shaft to rotate in a first direction in relation to the shell but prevent the shaft from rotating in a second direction, the ratchet mechanism including at least one pawl angled outwardly from an outer surface of the rotatable shaft and engageable with an at least one ratcheting aperture through an outer wall of the shell, said pawl comprising a ramp portion configured to disengage the pawl from the ratcheting aperture during relative axial movement of the shell and rotatable shaft;
wherein the outer diameter of the shaft and the inner diameter of the shell are selected such that as the shaft is rotated, while the suture anchor is implanted in the bone hole, the suture thread is drawn through the suture aperture of the shell and wraps onto the shaft thereby increasing the diameter on the shaft as the shaft is rotated, the wrapped suture thread coming into contact with the shell which is adapted to apply an outward force to the retaining portion to outwardly deform the retaining portion into contact with the wall of the bone hole and thereby increase an outer diameter of the shell along at least a portion of the length of the shell to a diameter larger than a diameter of the bone hole.

23. The knotless suture anchor of claim 22, further comprising a spring disposed in contact with the shaft and the shell to bias the two together into a predetermined position at which the ratchet mechanism will prevent rotation in the second direction.

24. The knotless suture anchor of claim 23, wherein the spring is disposed such that the shaft may be moved by a predetermined amount against the spring such that the ratchet mechanism is temporarily disengaged to permit rotation of the shaft in the second direction to loosen the suture thread.

25. The knotless suture anchor of claim 22, further comprising a tension indicator located at the shell in contact with the suture thread, wherein the tension indicator is adapted to visually indicate an amount of tension on the suture thread.

26. The knotless suture anchor of claim 22, wherein the shell comprises first and second suture thread guides disposed at the outer wall of the shell between the distal and proximal ends, the first and second suture thread guides being angularly separated from each other about the outer wall of the shell and each having a hole with a size that is large enough to receive a suture thread, the guide holes having a longitudinal axis that is substantially parallel to a longitudinal axis of the inner member, wherein the thread guides do not extend beyond either the distal or proximal ends of the shell.

27. The knotless suture anchor of claim 26, wherein the first and second suture thread guides are disposed one hundred and eighty degrees (180°) apart on the outer wall of the shell.

28. The knotless suture anchor of claim 26, further comprising a tension indicator located at one of said suture thread guides in contact with the suture, wherein the tension indicator is adapted to visually indicate an amount of tension on the suture.

29. The knotless suture anchor of claim 26, further comprising first and second suture thread guide channels, each of which is disposed in alignment with a respective suture thread guide between the suture thread guide and an aperture in the outer wall of the shell, each guide channel comprising a relieved portion of the outer wall of the shell having a depth selected so as to receive a suture thread, whereby a suture thread disposed in the knotless suture anchor is configured to be guided by the thread guides and guide channels to positions that are away from contact with surrounding bone.

30. The knotless suture anchor of claim 22, wherein as the suture thread is wrapped onto the shaft, the suture thread comes into contact with the retaining portion which thereby applies pressure to the wrapped suture thread to hold it in place on the shaft.

* * * * *